United States Patent [19]
Meagher et al.

[11] Patent Number: 5,755,967
[45] Date of Patent: May 26, 1998

[54] SILICALITE MEMBRANE AND METHOD FOR THE SELECTIVE RECOVERY AND CONCENTRATION OF ACETONE AND BUTANOL FROM MODEL ABE SOLUTIONS AND FERMENTATION BROTH

[76] Inventors: Michael M. Meagher, 3529 S. 76th St., Lincoln, Nebr. 68506; Nasibuddin Qureshi, Bldg. 16, Apt. 1619, 451 N. 44th St., Lincoln, Nebr. 68503; Robert Hutkins, 3415 S. 29th, Lincoln, Nebr. 68502

[21] Appl. No.: 735,283

[22] Filed: Oct. 22, 1996

Related U.S. Application Data

[60] Provisional application No. 60/018,129, May 22, 1996.

[51] Int. Cl.[6] .................................................. B01D 61/36
[52] U.S. Cl. ...................... 210/640; 210/651; 210/500.25
[58] Field of Search ................................. 210/640, 651, 210/500.25; 435/150, 160, 842; 502/4, 64

[56] References Cited

U.S. PATENT DOCUMENTS

| | | | |
|---|---|---|---|
| 4,925,562 | 5/1990 | Hennepe | 210/640 |
| 5,063,156 | 11/1991 | Glassner | 435/150 |
| 5,143,620 | 9/1992 | Chou | 210/640 |
| 5,385,647 | 1/1995 | Brueschke | 203/39 |
| 5,464,798 | 11/1995 | Jia | 502/64 |

OTHER PUBLICATIONS

Title: Preparation and Sparation Properties of Silcalite Composite Membranes J. Memb. Sci. 105 Year: 1995 Author Bai et al. pp. 79–87.

Tilte: Separation of Methanol/Methyl-Tert-Butyl Ether Mixture by Pervaporation Using Silcalite Membrane J. Memb. Sci. 107 Year: 1995 Author: Sano et al. pp. 193–196.

Title: Addition of Alumina to Cellulose Acetate Membranes J. Memb. Sci. 104 Year: 1995 Author: Wara et al. pp. 43–49.

Title: Separation of Tolene/Ethanol Mixture by Pervaporation Using Active Carbon–Filled Polymeric Membranes Separation Sci. Technol. 29 Years: 1994 Author: Duvac pp. 357–372.

Title: Zeolite Filled Silicone Rubber Membranes J. Memb. Sci. 89 Year: 1994 Author: Hennepe et al. pp. 185–196.

Title: Development of a Matrix–Matrix Membrane for Pervaporation Separation Sci. Technol. 29 Year 1994 Author: Okumus et al. pp. 2451–2473.

Title: Recovery of 2,3–Butanediol by Vacuum Membrane Distillation Separation Sci. Technol. 29 Year: 1994 Author: Qureshi et al. pp. 1733–1748.

Title: Separation of Ethanol/Water Mixture by Silicalite Membrane on Pervaporation J. Memb. Sci. Year:1994 Author: Sano et al. pp. 221–228.

Title: Pervaporation and Evaporation of a New Type of Ion Exchange Membrane J. Memb. Sci. Year: 1993 Author Simons et al. pp. 63–67.

Title: Pervaporation of Model Acetone–Butanol–Ethanol Fermentation Product Solutions Using Polytetrafluoroethylene Membranes Separation Sci. Technol. 28 Year: 1993 Author: Vrana et al. pp. 2167–2178.

Title: Sorption Isotherms of Alcohols in Zeolite–Filled silicone Rubber and in PVA–Composite Membranes J. Memb. Sci. 70 Years: 1992 Author Bartels–Caspers et al. pp. 75–83.

(List continued on next page.)

*Primary Examiner*—Ernest G. Therkorn
*Attorney, Agent, or Firm*—Suiter & Associates PC

[57] ABSTRACT

Silicalite, silicalite filled polymer membrane, and process for the selective adsorption of acetone and butanol from aqueous solutions thereof. The silicalite, silicalite filled polymer membrane, and process are particularly suited to the removal of acetone and butanol from *Clostridium acetobutylicum* fermentation media in that the membrane is not fouled by the fermentation media and may be used without removing the cells from the fermentation media. The silicalite and silicalite filled polymer membrane show excellent selectivity to the adsorption of acetone and butanol relative to the ethanol, acetic acid, and butyric acid components of the fermentation media.

63 Claims, 13 Drawing Sheets

OTHER PUBLICATIONS

Title: Preparation and Characterization of THin Film Zeolite-PDMS Composite Membrane J. Memb. Sci. 73 Year: 1992 Author: Jia et al. pp. 119–128.

Title: Continuous Acetone–Butanol–Ethanol (ABE) Fermentation Using Immobilized Cells of *Clostridium acetobutylicum* in a Packed Bed Reactor and Integration with Product Removal by Pervaporation Biotechnol. Bioeng. 38 Year: 1991 Author: Fiedl et al. pp. 518–527.

Title: The Acetone–Butanol–Ethanol Fermentation: Recent Progress in Technology Biotechnol. Gene. Engineering Rev. 7 Year: 1989 Author: Maddox pp. 189–220.

Title: Inline Toxic Product Removal During Solvent Production by Continuous Fermentation Using Immobilized *Clostridium acetobutylicum* Enz. Microbial Technol. 9 Year: 1987 Author: Ennis et al. pp. 672–675.

Title: Continuous Production of BUtanol from a Glucose/Xylose Mixture with an Immobilized Cell System Coupled to Pervaporation Biotechnol. Lett. 9 Year: 1987 Author: Groot et al. pp. 867–870.

Title: Zeolite–Filled Silicone Rubber Membranes J. of Memb. Sci. Year: 1987 Author: Hennepe et al. pp. 39–55.

Title: Sudy of Butanol Extraction Through Pervaporation in Acetobutylic Fermentation Biotechnol. Bioeng. 30 Year: 1987 Author: Larrayoz et al. pp. 692–696.

Title: Separation of Dilute Aqueous Butanol and Acetone Solutions by Pervaporation Through Liquid Membranes Biotechnol. Bioeng. 30 Year: 1987 Author: Matsumura et al. pp. 887–895.

Title: Pervaporation for Simultaneous Product Recovery in the Butanol/Isopropanol Batch Fermentation Biotechnol. Lett. 6 Year:1984 Author: Groot et al. pp. 709–714.

Title: Increase of Substrate Conversion by Pervaporation in the Continuous Butanol Fermentation Biotechnol. Lett. 6 Year: 1984 Author: Groot et al. pp. 789–792.

Title: Adsorption of Alcohols from Aqueous Solutions by ZSM–5 J. Chem. Technol. Biotechnol. 34A Year: 1983 Author: Milestone et al. pp. 73–79.

Title: Concentration of Alcohols by Adsorption on Silicalies J. Chem. Technol. Biotechnol. 31 Year: 1981 Author: Milestone et al. pp. 732–736.

Collins, "Where to Use Molecular Sieves," *Chem. Eng. Prog.*, vol. 64, pp. 66–71 (1968).

Ennis et al., "Use of *Clostridium acetobutylicum* P262 for Production of Solvents from Whey Permeate," *Biotechnol. Lett.*, vol. 7, pp. 601–606 (1985).

Jia et al., "Ceramic–Zeolite Composite Membranes and Their Application for Separation of Vapor/Gas Mixtures," *J. Memb. Sci.*, vol. 95, pp. 1–10 (1994).

Kesraoni–Ouki et al., "Natural Zeolite Utilization in Pollution Control: A Review of Applications to Metals' Effluents," *J. Chem. Technol. Biotechnol.*, vol. 59, pp. 121–126 (1994).

Mumpton, "Natural Zeolites: A New Industrial Mineral Commodity," in *Natural Zeolites: Occurance, Properties, and Use* (Sand et Al., Eds.) Permagon Press, pp. 8–9 (1976).

U.S. Dept. Of Energy, Office of Energy Research, Office of Program Analysis, "In Membrane Separation Systems," Contract No. DE–ACol–88ER30133, pp. 4–1 to 4–13 (Mar. 1990).

SILICALITE MEMBRANE AND METHOD FOR THE SELECTIVE RECOVERY AND CONCENTRATION OF ACETONE AND BUTANOL FROM MODEL ABE SOLUTIONS AND FERMENTATION BROTH

RELATED APPLICATIONS

This application claims priority under 35 U.S.C. § 119(e) based on Provisional application Ser. No. 60/018,129, filed May 22, 1996.

BACKGROUND OF THE INVENTION

1. Field of the Invention

The present invention relates to a new composite membrane and method for the recovery of acetone and butanol from aqueous solutions and, in particular, to an efficient method of recovering butanol from the *Clostridium acetobutylicum* acetone butanol ethanol (ABE) fermentation. This invention is particularly addressed to the problem of fouling of the silicalite membrane by the fermentation broth.

2. Description of the Prior Art

The present invention employs pervaporation, i.e., selective removal of a solvent. In a pervaporation method, molecules are selectively adsorbed by a membrane and are caused to diffuse across the membrane by a driving force such as a vacuum. The stumbling block to using this technology is that existing membranes do not have sufficient selectivity toward the desired species to be separated and/or sufficient flux rate.

Prior to the emergence of the petroleum and petrochemical industry, all of the acetone and butanol produced was made using *Clostridium acetobutylicum* fermentation. However, commercial production of butanol by fermentation and distillative recovery is now considered cost prohibitive and cannot compete with petroleum-based acetone and butanol production.

Because the fermentation product is highly toxic to the culture, the acetone butanol ethanol concentration achieved in the fermentation beer is less than 20 g/L. Methods of acetone butanol ethanol recovery investigated during the last decade are documented tby Maddox, "The acetone-butanol-ethanol fermentation: recent progress in technology," *Biotechnol. Gene. Eng. Rev.* 7 (1989) 189–220. Among the methods, pervaporation has several advantages in that it does not have any harmful effects on the microorganisms, does not remove medium ingredients from the reaction mixture, and results in a comparatively concentrated product stream.

The removal of butanol from fermentation broth by pervaporation using silicone membranes is known in the art, see, e.g., Groot et al., "Pervaporation for simultaneous product recovery in the butanol/isopropanol batch fermentation," *Biotechnol. Lett.* 6 (1984) 709–714; Groot et al., "Increase of substrate conversion by pervaporation in the continuous butanol fermentation," *Biotechnol. Lett* 6 (1984) 789–792;, Groot et al., "Continuous production of butanol from a glucose/xylose mixture with an immobilized cell system coupled to pervaporation," *Biotechnol. Lett.* 9 (1987) 867–870; and Larrayoz et al., "Study of butanol extraction through pervaporation in acetobutylic fermentation," *Biotechnol. Bioeng.* 30 (1987) 692–696. The use of polypropylene membranes is also known, see, e.g., Friedl et al., "Continuous acetone-butanol-ethanol (ABE) fermentation using immobilized cells of *Clostridium acetobutylicum* in a packed bed reactor and integration with product removal by pervaporation," *Biotechnol. Bioeng.* 38 (1991) 518–527 Matsumura et al., "Separation of dilute aqueous butanol and acetone solutions by pervaporation through liquid membranes," *Biotechnol. Bioeng.* 30 (1987) 887–895 disclose the use of a polypropylene membrane with oleyl alcohol filled into the pores thereof. However, the membrane disclosed therein is not stable, inasmuch as the oleyl alcohol is taught to diffuse out of the membrane.

Unfortunately, few reports exist on the development of high flux, high selectivity, stable membranes to remove butanol. In 1990, a study by the Department of Energy ranked pervaporation as the number one priority among 38 possible areas of membrane research, stating that "If sufficiently selective membranes could be made, pervaporation could replace distillation in many separations." U.S. Dept. of Energy, Office of Energy Research, Office of Program Analysis. In Membrane Separation Systems. Contract No. DE-ACo1–88ER30133. Vol 1, March 1990, pp. 4–12.

Silicalites, also known as zeolites, are molecular sieves and have capabilities to adsorb organic solvents, such as ethanol, propanol, methanol, acetone, butanol, etc., from aqueous solutions. During recent years, there has been an interest in the development of zeolite filled membranes for various separations. For example, it is known to include silicalites in silicone membranes to improve ethanol, methanol, and propanol flux and selectivity. See te Hennepe et al., "Zeolite-filled silicone rubber membrane. Part I. Membrane pervaporation and pervaporation results," *J. Memb. Sci.* 35(1987) 39–55, which teaches that a silicone rubber membrane filled with 70% silicalite by weight resulted in an ethanol selectivity of 19 and a flux of 0.058 L/m²h, compared to an ethanol flux and selectivity of 7 and 0.023 L/m²h, respectively, when no silicalite was present.

Jia et al., "Preparation and characterization of thin film zeolite-PDMS composite membrane," *J. Memb. Sci.* 73(1992) 119–128, employed a similar approach in preparing a membrane of silicone rubber filled with silicalite particles to remove ethanol from model solutions. The silicalite-1 employed by Jia et al. differs from that of the present invention in that the silicalite particle size of Jia et al. is smaller. Jia et al. report an increase of selectivity of ethanol from 4.4 to 34 and a flux decrease from 530 to 150 g/m²h when the silicalite filling was increased from 0% to 77%. The membrane was operated in continuous mode for 3800 minutes and both selectivity and flux were found to be decreasing with time.

Other authors who have used similar approaches of filling either silicalite or activated carbon into polymeric membranes to remove ethanol from model solutions are: te Hennepe et al., "Zeolite filled silicone rubber membranes: experimental determination of concentration profiles," *J. Memb. Sci.* 89 (1994) 185–196; Duval et al., "Separation of toluene/ethanol mixture by pervaporation using active carbon-filled polymeric membranes," *Separation Sci. Technol.* 29 (1994) 357–373 (separating toluene/ethanol mixtures); Okumus et al., "Development of a matrix-matrix membrane for pervaporation," *Separation*7 Sci. Technol. 29 (1994) 2451–2473 (using zeolite filled cellulose acetate membrane to separate an ethanol/water mixture); Jia et al., "Ceramic-zeolite composite membranes and their application for separation of vapor/gas mixtures," *J. Memb. Sci.* 95 (1994) 1–10 (separating gases); Sano et al., "Separation of ethanol/water mixture by silicalite membrane on pervaporation," *J. Memb. Sci.* 95 (1994) 221–228; Bai et al., "Preparation and separation properties of silicalite composite membranes," *J. Memb. Sci.* 105 (1995) 79–87 (separating gases); and Sano et al., "Separation of methanol/methyltert-butyl ether mixture by pervaporation using silicalite membrane," *J. Memb. Sci.* 107 (1995) 193–196. The prior art shows that zeolite filled membranes show improved ethanol selectivities, and thus better separation of ethanol/water mixtures, over silicone or cellulose acetate membranes.

Other fillers which have been tested for the different separation systems include alumina (Wara et al., "Addition of alumina to cellulose acetate membranes," *J. Memb. Sci.* 104 (1995) 43–49); active carbon (Duval et al.; *Separation Sci. Technol.* 29 (1994) 357–373, supra, for toluene/ethanol separation); silicalite (Sano et al., *J. Memb. Sci.* 107 (1995) 193-196 supra, for methanol/methyl-tert-butyl ether separation); silicalite (te Hennepe et al., *J. Memb. Sci.* 89 (1994) 185–196, supra, for propanol separation); silicalite (Jia et al., *J. Memb. Sci.* 95 (1994) 1–10, supra, for $CH_3OH/H_2$ and $CH_3OH/CH_4$ separation); silicalite (Bai et al., *J. Memb. Sci.* 105 (1995) 79–87, supra, for separation of gases); zeolite (Bartels-Caspers et al., "Sorption isotherms of alcohols in zeolite-filled silicone rubber and in PVA-composite membranes," *J. Memb. Sci.* 70 (1992) 75–83); and ion exchange microporous Celgard K-273 (Simons et al., "Pervaporation and evaporation of a new type of ion exchange membrane," *J. Memb. Sci.* 78 (1993) 63–67).

In te Hennepe et al., U.S. Pat. No. 4,925,562, a pervaporation membrane and process employing a membrane comprising a zeolite embedded on a silicone rubber polymer matrix is disclosed.

The silicalite according to the present invention is suitable for acetone, butanol arid ethanol removal and also is suitable filler in silicone or other polymer membranes. The silicalite of the present invention is different than the silicalite made by te Hennepe et al., *J. Memb. Sci.* 35 (1987) 39–55, supra; Jia et al., *J. Memb. Sci.* 73 (1992) 119–128, supra; Jia et al., *J. Memb. Sci.* 95 (1994) 1–10, supra; and Sano et al., *J. Memb. Sci.* 95 (1994) 221–228, supra. The silicalite of the present invention does not adsorb ethanol more than 1–2 mg/g. It adsorbs acetone 8–12 mg/g and butanol 85–90 mg/g selectively. The silicalite membrane of the present invention differs from those of te Hennepe et al., *J. Memb. Sci.* 35 (1987) 39–55, supra, who teach that ethanol selectivity improved from 7.6 to 25; Jia et al., *J. Memb. Sci.* 73 (1992) 119–128, supra, who teach that ethanol selectivity increased from 4.4 to 34; and Sano et al., *J. Memb. Sci.* 95 (1994) 221–228, supra, which teaches that ethanol selectivity improved to 60. Under identical conditions of feed ethanol concentration and temperature, our ethanol selectivity was not more than 1.39 (Table 12).

In addition to the poor flux and selectivity of the prior art membranes, another problem with the use of the prior art membranes in a fermentation process is fouling caused by the fermentation broth.

It is, therefore, an object of the present invention to provide an improved pervaporation membrane and process that will allow acetone and butanol to be produced at a significantly lower cost from renewable resources.

Another object of the present invention is to provide an improved membrane and pervaporation process for the separation and/or concentration of butanol and acetone from fermentation broth, as well from model solutions and fermentation media, with excellent selectivity and flux rates.

Another object of the invention is to provide a membrane that is not affected by the fermentation broth, and thus, is reusable and may be used continuously for long periods without degradation of performance.

Other objects and advantages of the present invention will become apparent from a consideration of the ensuing description and drawings.

SUMMARY OF THE INVENTION

The objects of the present invention are provided by the novel silicalite membrane of the present invention and the pervaporation method employing such membrane.

The present invention can be considered an improvement over the art known processes in the high degree of selectivity toward acetone and butanol that is achieved and the excellent flux rate.

Selectivity is defined as the ratio of the butanol:water concentration of the permeate to that of the retentate:

$$\text{selectivity} = \text{permeate } (C_{butanol}/C_{water})/\text{retentate } (C_{butanol}/C_{water})$$

where permeate is what crosses the membrane and the retentate is the feed stock concentration or, what is retained by the membrane.

It has been found that, in accordance with the present invention, selectivities of about 100 to about 150, or higher can be achieved, and fluxes of about 90 $g/m^2h$ to about 200 $g/m^2h$ can be achieved using the composite membrane of the present invention which comprises silicalite particles in a polysiloxane elastomer (silicone) membrane.

DETAILED DESCRIPTION OF THE INVENTION

There are two steps involved in the removal of volatiles by pervaporation. One is the sorption of the volatile into the membrane and the other is its diffusion through the membrane due to concentration gradient created by the driving force either vacuum or sweep gas. In the present studies we used vacuum due to its larger driving force and because it gives higher flux. To enhance the membrane performance, selective sorption of the volatile must be increased and diffusion resistance must be reduced, or both. By filling silicalite into the membrane, we have attempted the first approach, i.e., increased the selective sorption. Because the diffusion is a function of the concentration of volatile in the membrane, a higher solubility also affects the diffusion. The filler we used has three characteristics for butanol and acetone: (1) it adsorbs them selectively in higher concentration, (2) it adsorbs them quickly and (3) it is hydrophobic in nature and thus, does not adsorb water. The first characteristic increases selectivity and increases concentration inside the membrane thereby affecting the diffusion, and the second characteristic results in increased flux. In addition to the above requirements, the energy of adsorption should be low enough to allow for desorption under operational conditions. If desorption does not occur because of the extra resistance caused by the adsorbent, flux will decrease.

The increased sorption of volatiles does not mean a higher saturation concentration in the polymer. During pervaporation the driving force keeps removing the volatile from the membrane. As the concentration of the volatile decreases in the membrane it adsorbs from the feed. The feed side concentration of the volatile is maintained at the same level over a larger part of the membrane. In a silicalite filled membrane butanol/acetone is adsorbed and desorbed by the subsequent silicalite particles and their path leads straight through the silicalite pores, te Hennepe et al., *J. Memb. Sci.* 35 (1987) 39–55, supra. Being hydrophobic in nature, the silicalite particles prohibit the water particles from entering the silicalite pores. This results in the tortuous path for the water molecules around the silicalite particles and decrease water flux.

Selective sorption, hydrophobicity, and higher solvent concentration inside the membrane are responsible for higher selectivity and faster sorption and straight path of the solvent inside the membrane are responsible for higher butanol flux.

Figure 8:
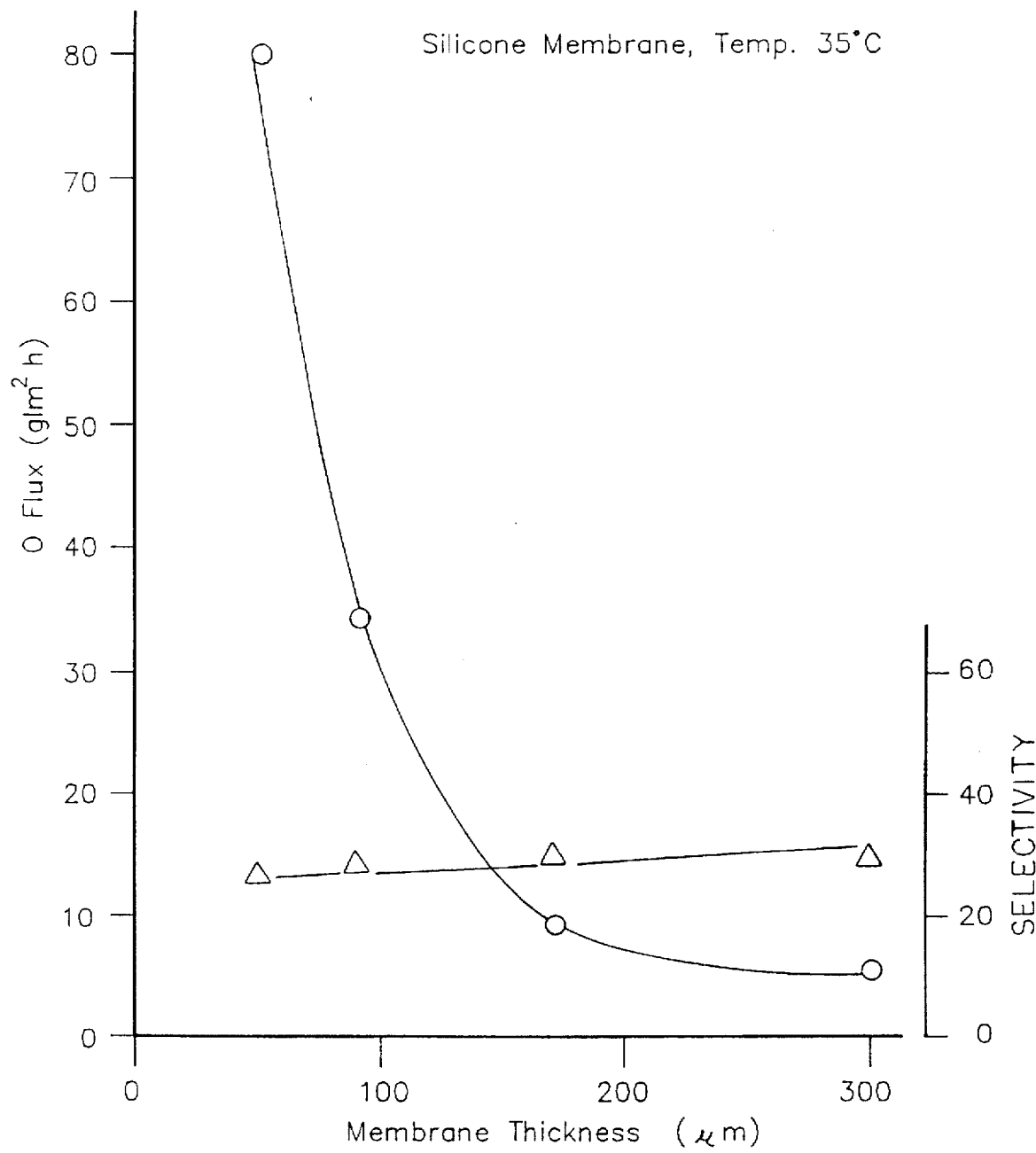
FIG. 8 shows the effect of membrane thickness on butanol flux and selectivity using a model 10 g/L butanol solution and a silicone membrane at 35° C. (wherein △=selectivity and ○=flux).
Figure 10:
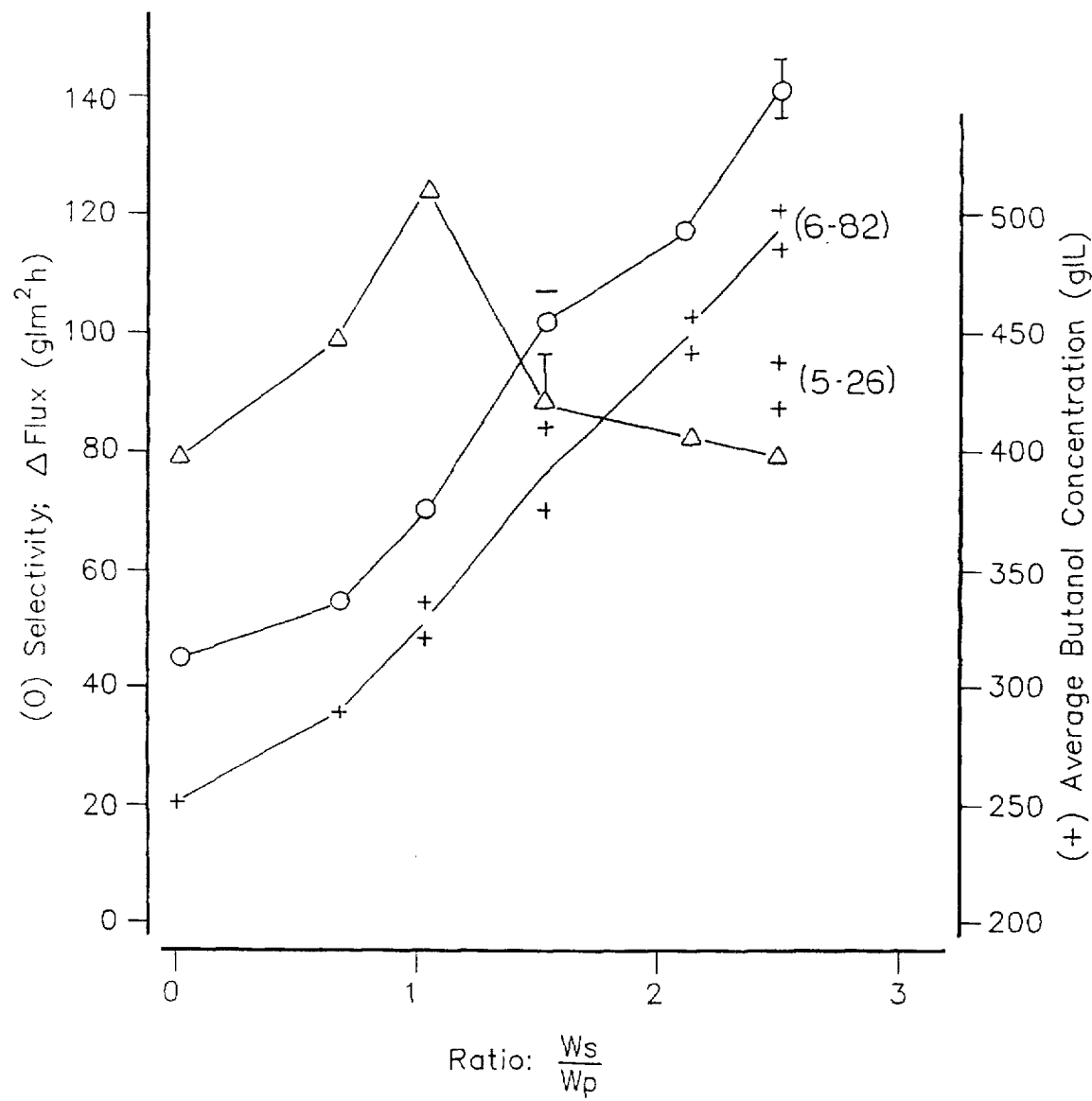
FIG. 10 shows the effect of silicalite content in the membrane on butanol selectivity and flux (wherein ○=selectivity, △=flux, and +=pervaporate butanol concentration). 6.82 and 5.26 are feed butanol concentrations at these points.
Figure 14:
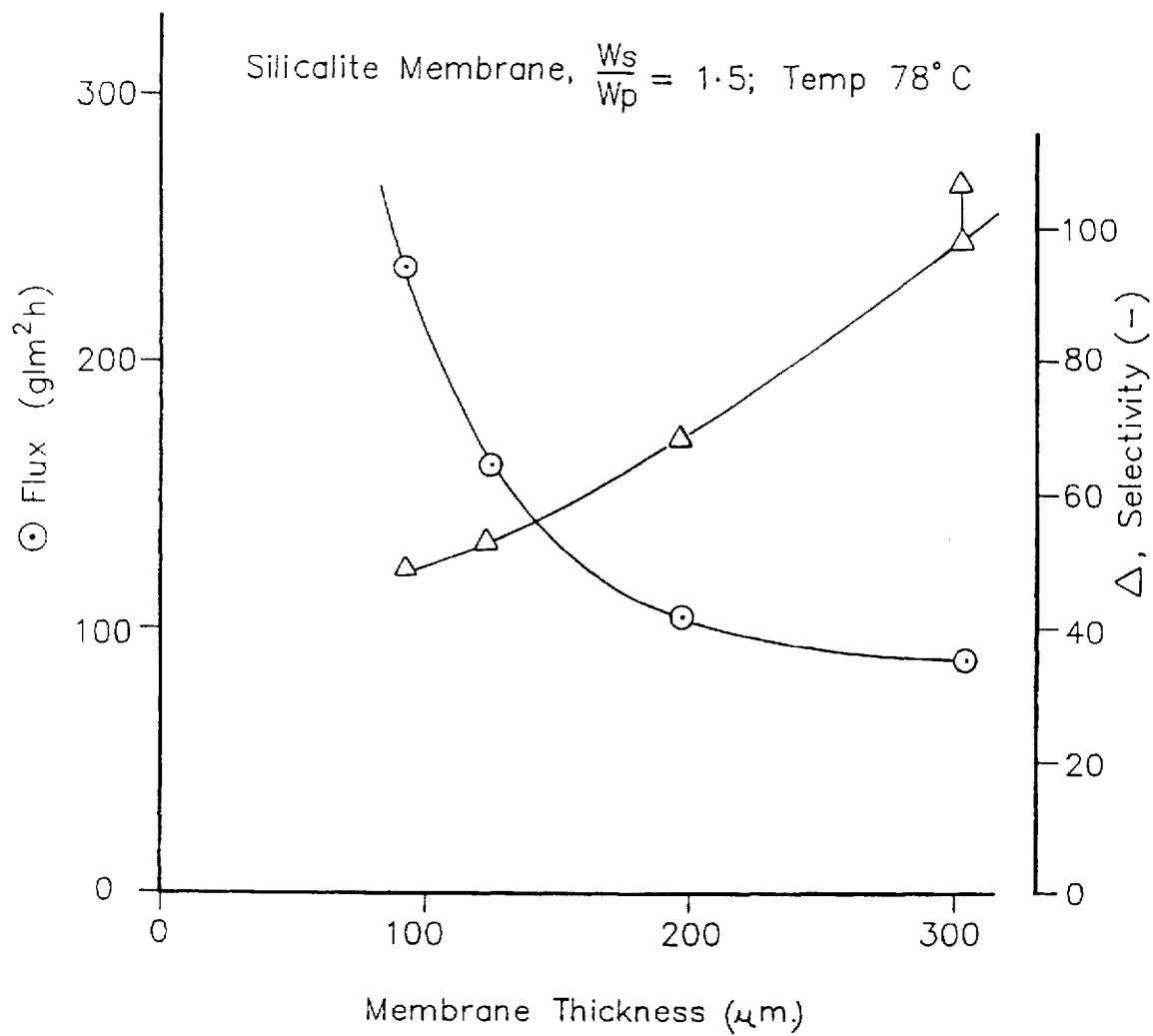
FIG. 14 shows the effect of membrane thickness on butanol flux and selectivity where butanol removal is by pervaporation using a silicalite membrane (wherein Δ=selectivity and ⊙=flux).

FIG. 10 shows the effect of silicalite content on butanol selectivity and flux. The temperature of operation was 78° C. and butanol concentration on the feed side was less than 10 g/L. As the silicalite content increased the selectivity increased. Flux increased up to Ws/Wp of 1.0 and then decreased (wherein Ws is the weight of silicalite and Wp is the weight of polymer in the membrane). The flux decreased due to increased membrane thickness. Experiments conducted at higher membrane thickness show lower flux (FIGS. 8 and 14).

Figure 7:
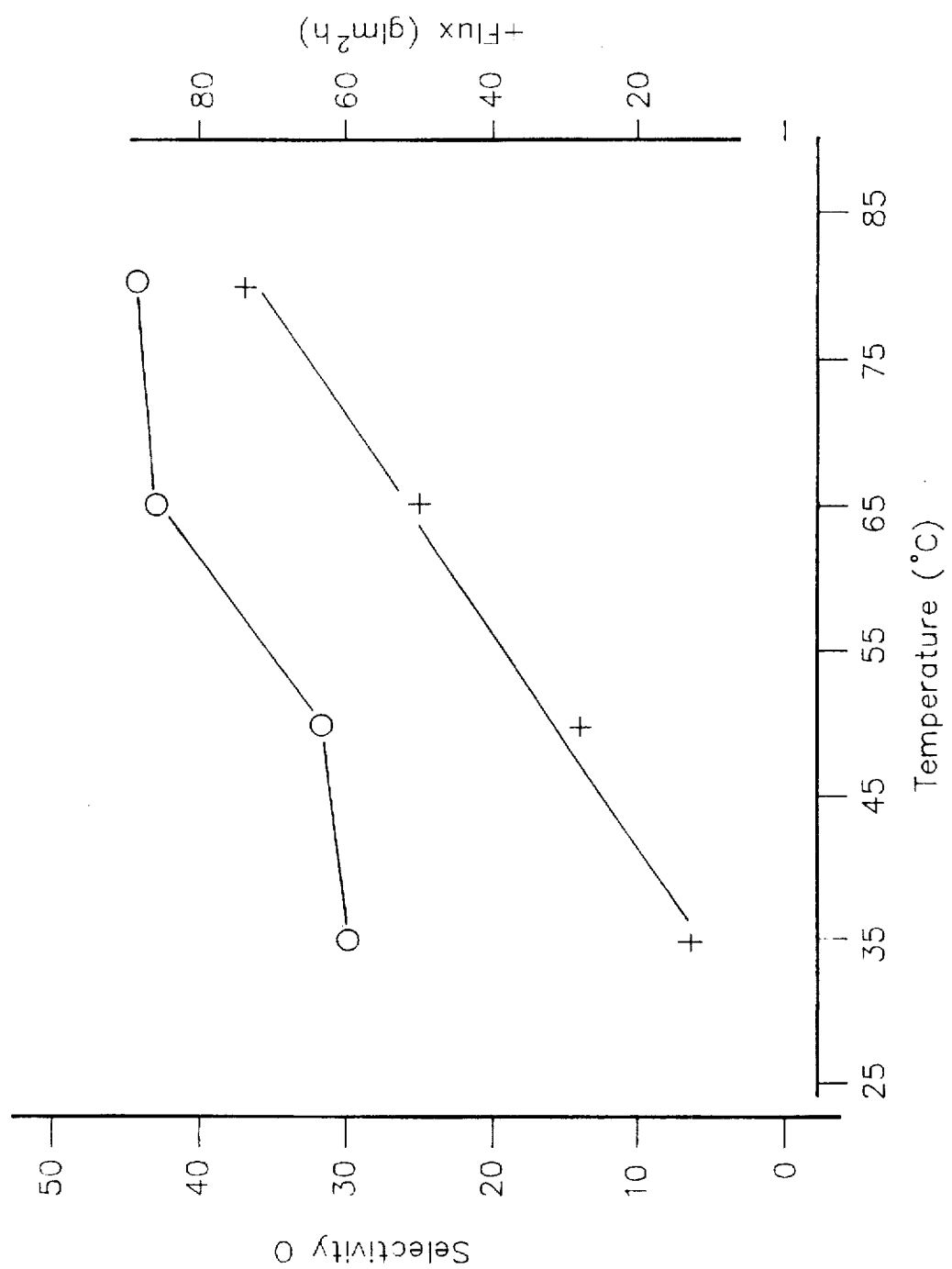
FIG. 7 shows the effect of temperature on flux using a model 10 g/L butanol solution and a silicone membrane (wherein ○=selectivity and +=flux).
Figure 11:
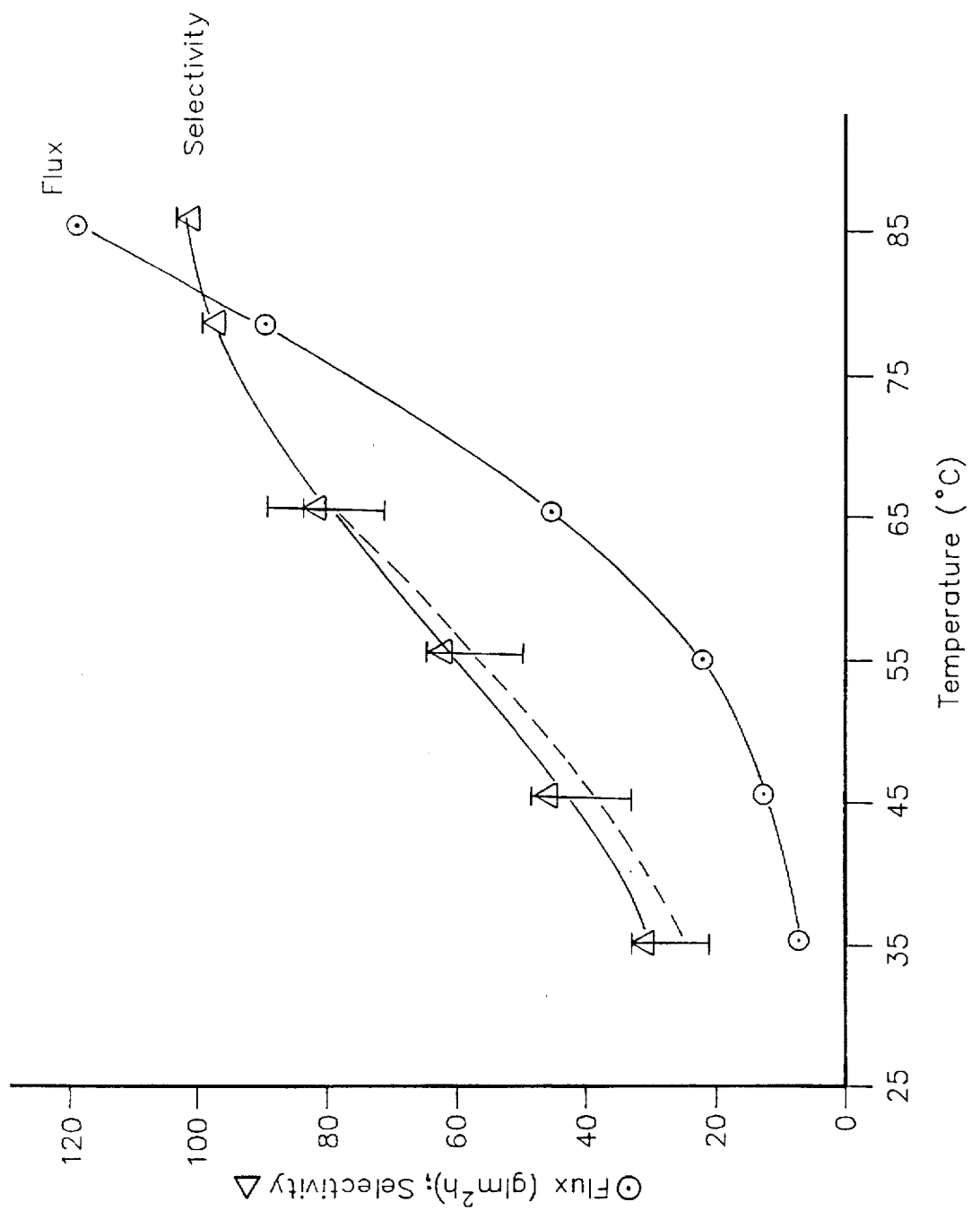
FIG. 11 shows the effect of operation temperature on butanol selectivity and flux of butanol removal by pervaporation using a silicalite membrane (wherein Δ=butanol selectivity and ⊙=flux).

Experiments were conducted to study the influence of temperature on flux and selectivity. As expected the flux increased with temperature due to the higher vapor pressure of the components of the feed resulting in an increase in driving force. FIG. 7 and FIG. 11 show an increase in the flux. In both the cases, the selectivity also increased with the increase in temperature.

In the case of silicalite membrane where the selectivity increase is proportional to the temperature increase, the selectivity increased because at higher temperature (78° C.), adsorption of butanol onto silicalite is not affected. However, te Hennepe et al., *J. Memb. Sci.* 35 (1987) 39–55, supra, reported an increase in ethanol flux and a decrease in selectivity with increase in temperature. In this case, this was due to lower sorption of ethanol at higher temperature.

Figure 15:
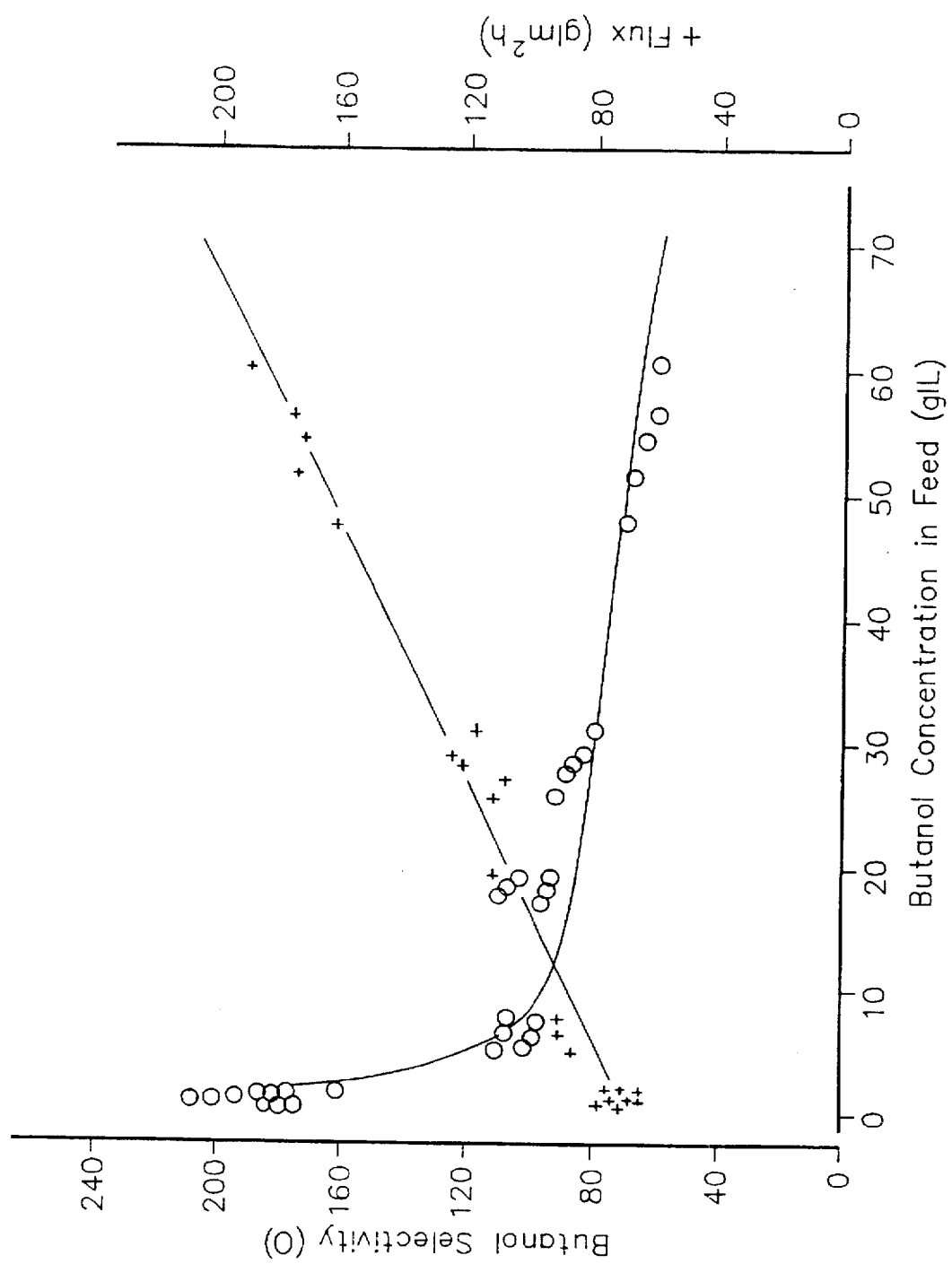
FIG. 15 shows removal of butanol from an aqueous butanol solution by pervaporation using a silicalite membrane (wherein ○=selectivity and +=flux).

The dependence of flux and selectivity on feed butanol concentration is shown in FIG. 15. Flux increases as the concentration of butanol increases in the feed. The flux increase is caused by the higher butanol concentration inside the membrane. A similar trend was observed by te Hennepe et al., *J. Memb. Sci.* 35 (1987) 39–55, supra, for ethanol flux. At this time, it is not understood why butanol selectivity was higher at lower butanol concentrations (<2 g/L) and lower at higher butanol concentrations (10–75 g/L). However, a similar trend was observed by Sano et al., *J. Memb. Sci.* 95 (1994) 221–228, supra, in the separation of ethanol using a silicalite membrane. At about 30 g/L retentate ethanol, selectivity was about 66 and at 700 g/L retentate ethanol, it was 18.

The following Example illustrates the method of pervaporation according to the present invention.

EXAMPLE 1

PERVAPORATION EXPERIMENTS

Figure 1:
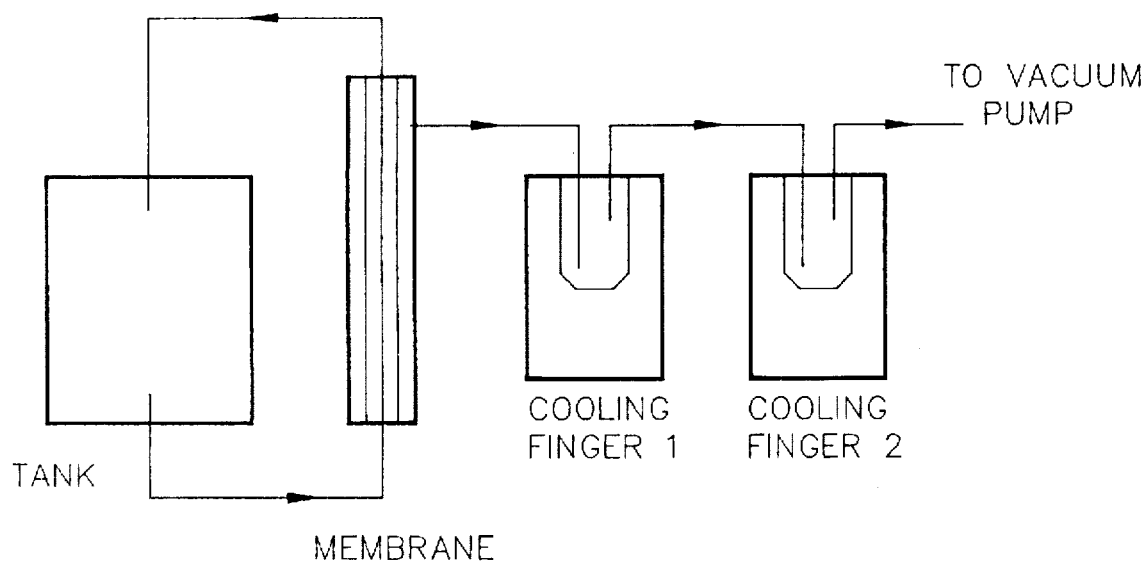
FIG. 1 shows a schematic diagram of pervaporation apparatus for acetone butanol ethanol removal.

A schematic diagram of pervaporation apparatus is shown in FIG. 1. The pervaporation apparatus included membrane supporting plates, a heat exchanger, a liquid circulating pump, a water bath, liquid nitrogen holders, cooling fingers and a vacuum pump. Two membranes of total membrane area of 0.022 m² were used. Details of the membrane module (Biorecovery Inc., Norwood, N.J.) have been given previously, see Vrana et al., "Pervaporation of model acetone-butanol-ethanol fermentation product solutions using polytetrafluoroethylene membranes," *Separation Sci. Technol.* 28 (1993) 2167–2178, and Qureshi et al., "Recovery of 2,3-butanediol by vacuum membrane distillation," *Separation Sci. Technol.* 29 (1994) 1733–1748, both of which are hereby incorporated by reference in their entirety. Model solution or fermentation broth was circulated at a flow rate of 2.8 L/minute using either a varistaltic pump (Manostat varistaltic pump, New York, N.Y.) or a Dayton pump (Dayton Electric Manufacturing Co., Chicago, Ill.). The inlet and outlet pressures were 4.0 and 1.0 psig, respectively. A stainless steel heat exchanger and auto control water bath were used to heat the retentate to the desired temperature (35–85° C.). The vapors of ABE were pulled through the membrane using a vacuum pump (Welch Duo-Seal vacuum pump, Sergent-Welch Scientific Co., Skokie, Ill.). The vacuum pump had a capability of creating vacuum up to 0.1 torr (0.1 mm Hg). An electronic vacuum gauge was used to measure the vacuum. Usually, vacuum readings were between 1 and 4 torr. The vacuum tubing used to connect the membrane and the vacuum pump was stainless steel (19 mm stainless steel Swagelok vacuum tubing). Two liquid nitrogen traps were used to condense ABE vapors (Kontes, 500 mL and 250 mL capacity; liquid nitrogen temperature −196° C.). Two liter capacity thermos flasks were used to cool the traps. Details of the membrane and operational conditions are given in Table 1.

TABLE 1

Details of membrane, pervaporation apparatus, and analytical conditions.

Membranes

| | |
|---|---|
| Membrane made of: | Silicone rubber and silicalite |
| Two membranes of sizes: | 154 × 72 mm |
| Total membrane area: | 0.022 m$^2$ |
| Membrane thickness: | 50–434 μm |
| Recovery temperature: | 35–85° C. |
| Feed circulation rate: | 2–2.8 L/min |
| Vacuum: | 2–4 mm Hg |
| ABE vapor condensation temperature: | −196° C. |

GC analyses

| | |
|---|---|
| Injector temperature: | 220–250° C. |
| Detector temperature: | 350° C. |

Column temperature

| | |
|---|---|
| Initial temperature: | 80° C. |
| Initial time: | 2 min |
| Rate: | 30° C./min |
| Final temperature: | 200° C. |
| Final time: | 1.5 min |

400 mL model solution or fermentation broth in a 500 mL conical flask was used to circulate through the membrane. On the top of this flask, a condenser was used to condense any volatiles and return them to the flask. After steady state had been reached (usually it took 1–1.5 hours), the condensed sample was thawed and weighed up to two decimal places on a balance. The flux and selectivity were calculated as follows:

$$Flux = W/(At) \ g/m^2 h$$

$$Selectivity = [y/(1-y)]/[x/(1-x)]$$

where W is weight of the condensate, A is membrane area in m$^2$, t is time in hours during which a sample was taken, y is weight fraction of butanol or acetone in permeate and x is weight fraction of butanol/acetone in retentate.

The following example is illustrative of making the silicone membrane (not containing silicalite).

EXAMPLE 2

SILICONE MEMBRANE MAKING

The silicone membranes were prepared from RTV 615A (dimethylsiloxane) and RTV 615B ( initiator) (General Electric Co.). 10 g RTV 615A and 1 g RTV 615B were mixed with 15–20 ml iso-octane in a glass beaker using a stirrer. The solution was mixed thoroughly and precaution was taken to avoid air bubbles. This homogeneous solution was poured onto a teflon plate and spread mechanically to form a thin liquid layer. The plate was kept at 75° C. in an oven for 10–20 hours to dry the membrane and to crosslink. After the membrane was cured, it was peeled off the plate and cut to the size of the pervaporation plate (154 mm×72 mm). The thickness of the membranes ranged from 50–300 μm. The membrane thickness was measured with a battery operated micrometer. These membranes were characterized for flux, selectivity, and temperature and thickness effects using model ABE solution, fermentation media, and actual fermentation broth.

CHARACTERIZATION OF SILICONE MEMBRANE IN MODEL BUTANOL (10 g/L) SOLUTION

Figure 2:
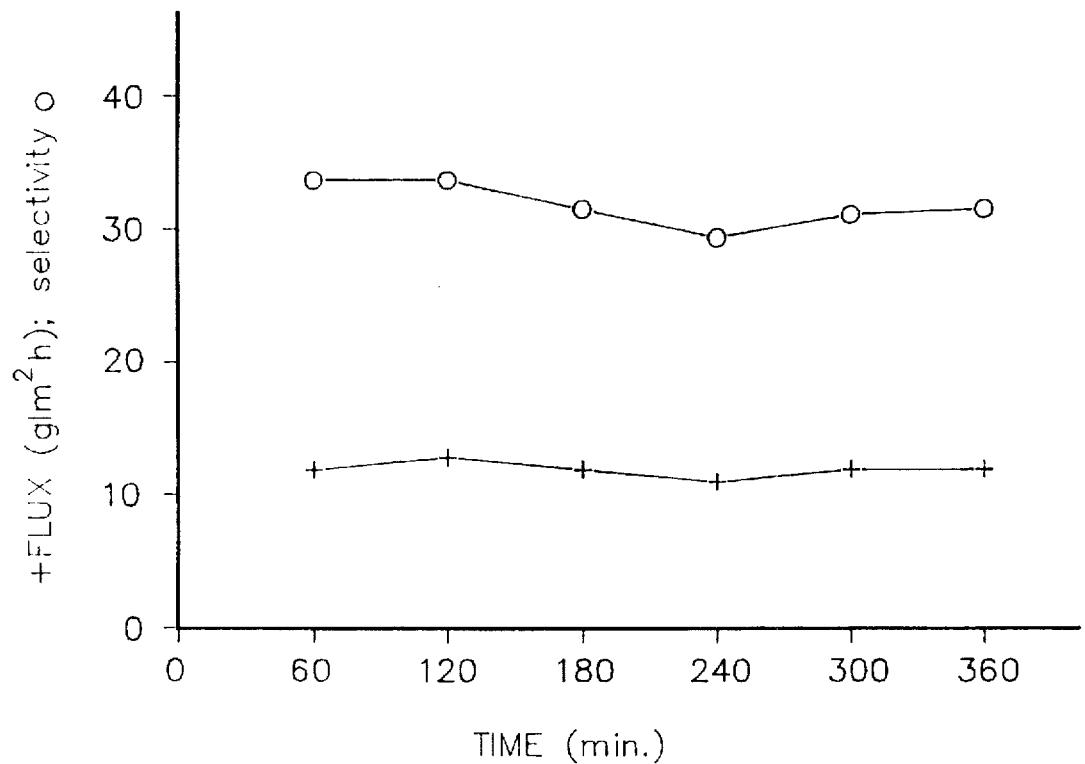
FIG. 2 shows selectivities and fluxes for butanol removal by pervaporation using a silicone membrane and model solution containing butanol at 10 g/L (wherein ○=selectivity and +=flux).

Initially, silicone membranes (i.e., without silicalite added) were made and characterized for their flux and selectivities. The model solution used contained butanol at 10 g/L. The selectivities and fluxes of butanol solution are shown in FIG. 2. Butanol selectivity varied between 28.5 to 32 and flux was 12.5 g/m$^2$h. The temperature of operation was 35° C.

SELECTIVITY AND FLUX EXPERIMENTS USING SILICONE MEMBRANE AND VARIOUS BUTANOL CONCENTRATIONS

Figure 3:
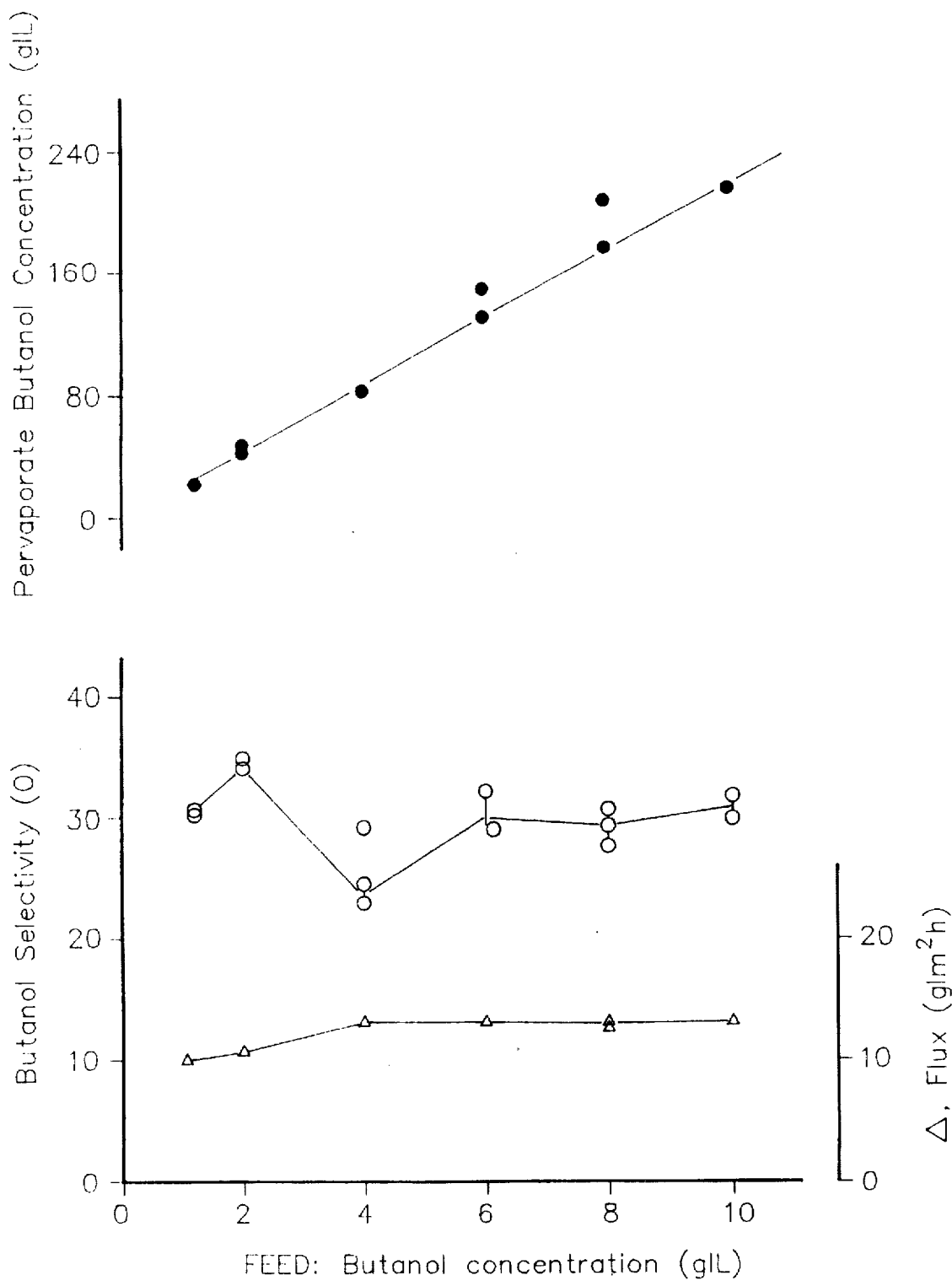
FIG. 3 shows the selectivity, flux, and butanol concentration in pervaporation permeate using silicone membrane and model solutions containing butanol in concentrations of 2, 4, 6, 8, and 10 g/L (wherein ○=butanol selectivity, △=flux, and ●=pervaporate butanol concentration).

Further experiments were run with various butanol concentrations in the feed medium. The concentrations of butanol in the model solution were 2, 4, 6, 8, and 10 g/L. The selectivity, flux, and butanol concentration in permeate are plotted in FIG. 3. Between the concentration range of 2 to 10 g/L, selectivity remained around 30 and butanol concentration in the permeate varied from 32 to 230 g/L.

SELECTIVITY AND FLUX EXPERIMENTS USING SILICONE MEMBRANE AND FERMENTATION MEDIA

Figure 4:
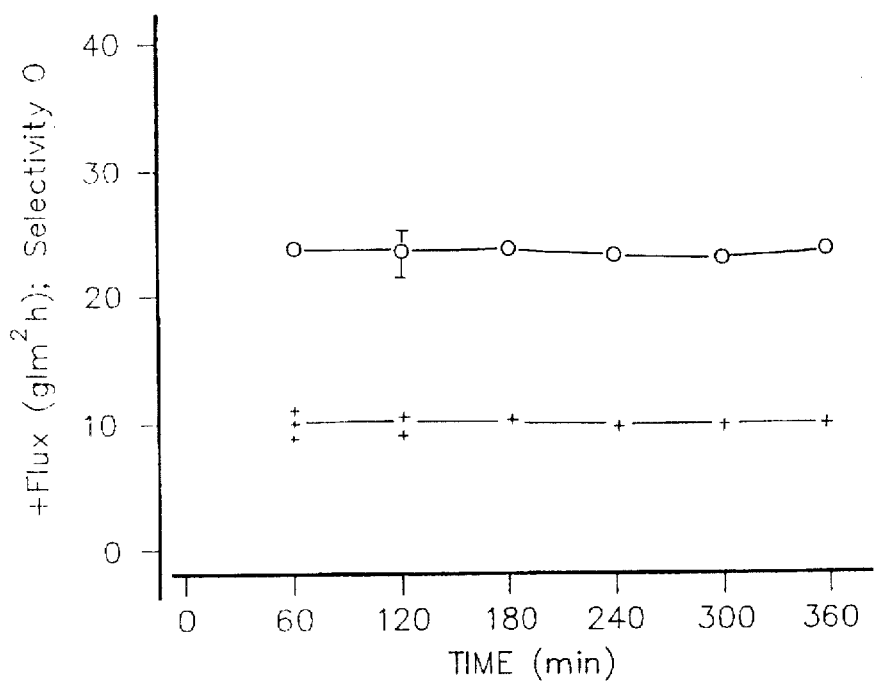
FIG. 4 shows the selectivity and flux of a model 10 g/L butanol solution in fermentation medium using silicone membrane (wherein ○=selectivity and +=flux).

Fermentation media are complex in nature and they tend to reduce flux and selectivities. To investigate this, a model 10 g/L butanol solution in fermentation medium was prepared, see Ennis et al., "Use of Clostridium acetobutylicum P262 for production of solvents from whey permeate," Biotechnol. Lett. 7 (1985) 601–606, herein incorporated by reference in its entirety. The pH of this medium was adjusted to 6.5. This medium/model solution was used to pervaporate butanol. The butanol selectivities remained between 28 and 28.5 and butanol flux was 12.5 g/m$^2$ h as shown in FIG. 4. Similarly, butanol selectivity in model solution (without fermentation medium) was 28.5 to 32. This clearly shows that butanol selectivity was not affected significantly by the fermentation medium used. The experiment was operated for 360 minutes under steady state conditions.

SELECTIVITY AND FLUX EXPERIMENTS USING SILICONE MEMBRANE AND FERMENTATION BROTH

Figure 5:
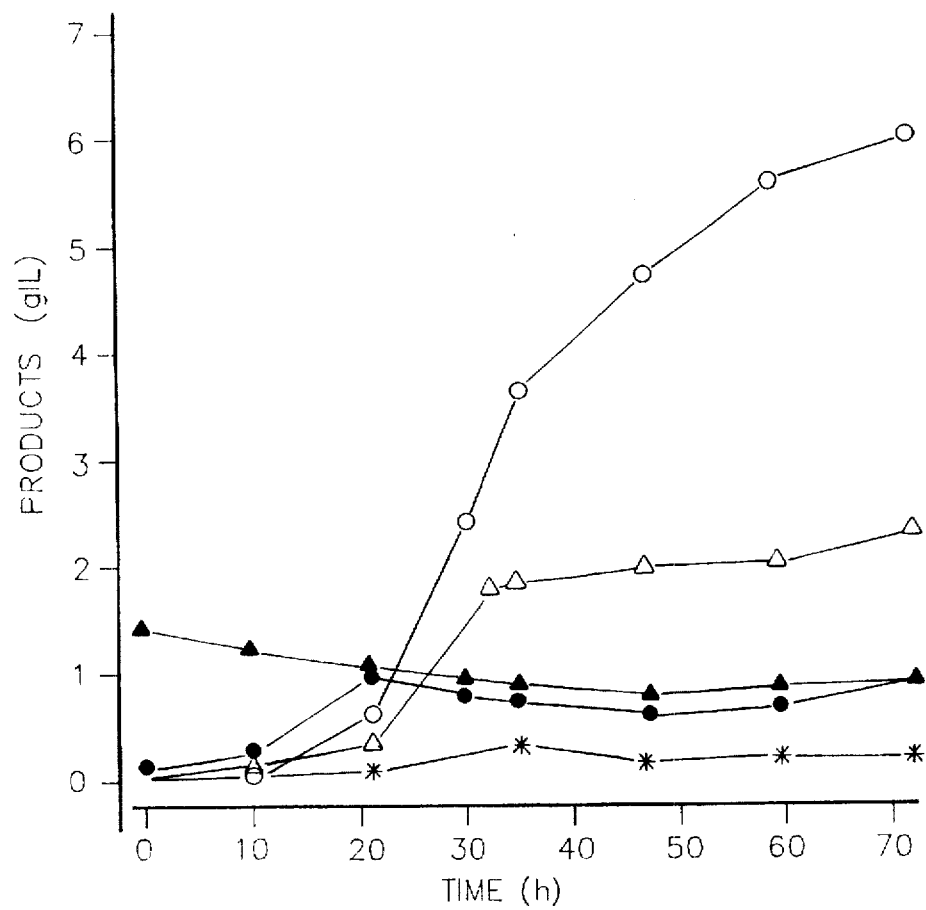
FIG. 5 shows the fermentation profile of acetone butanol ethanol production from glucose by *Clostridium acetobutylicum* ATCC 824 in a batch reactor (wherein △=acetone, ○=butanol, *=ethanol, ▲=acetic acid, and ●=butyric acid).

Next, the silicone membrane was tested in fermentation broth. Acetone butanol ethanol fermentation was run to produce ABE and to check flux and selectivities. The composition of fermentation medium and conditions of fermentation are given below in Example 5. The fermentation was run for 72 hours and it produced acetone 2.3 g/L, butanol 6 g/L, ethanol 0.2 g/L and acetic and butyric acid at 1.0 g/L each. The total solvents in the fermentation broth were 8.5 g/L. FIG. 5 shows fermentation profile of acetone butanol ethanol production in a batch reactor.

Figure 6:
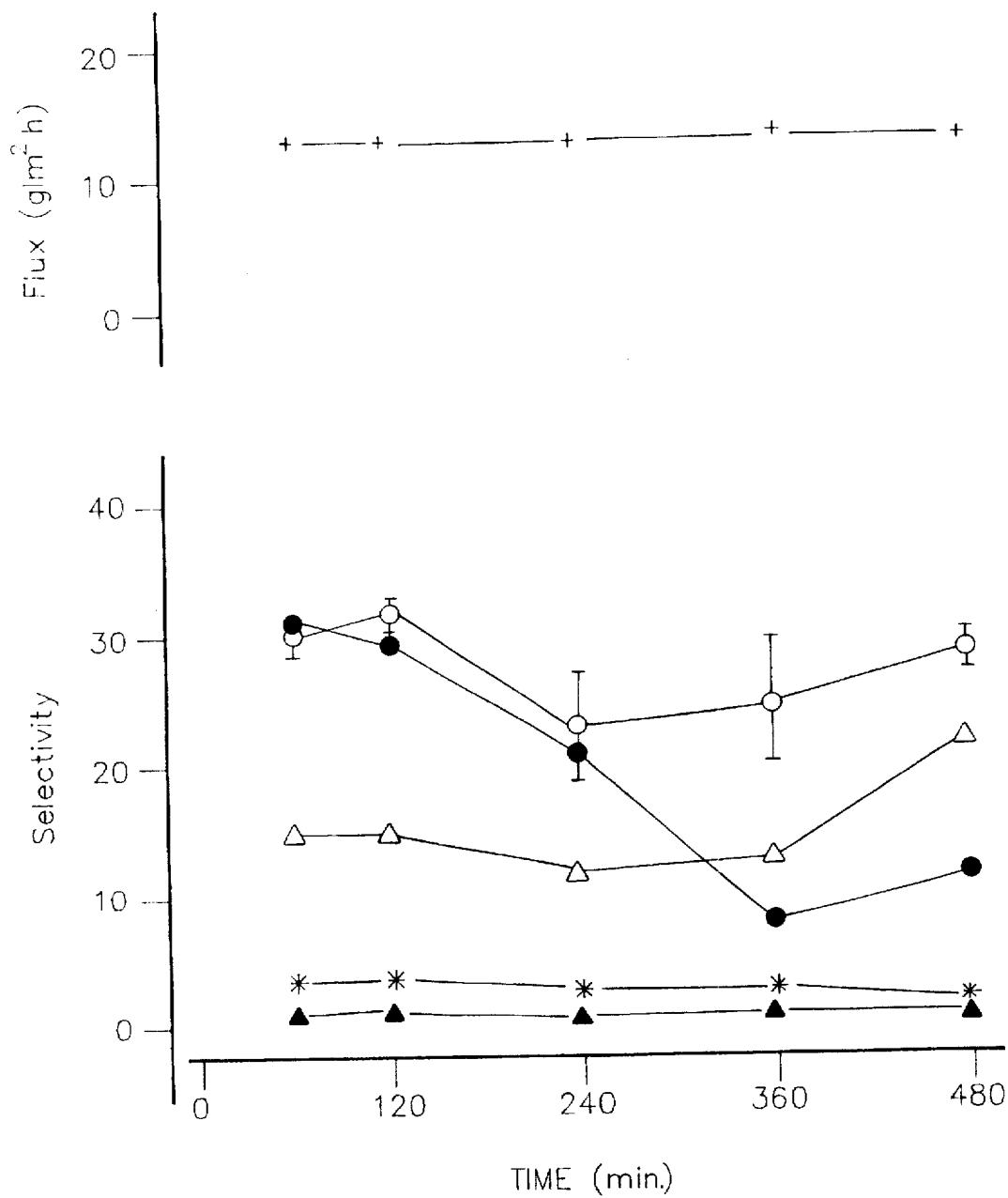
FIG. 6 shows total flux and selectivities of all the components of ABE fermentation products using silicone membrane (wherein +=flux, △=acetone, ○=butanol, *=ethanol, ▲=acetic acid, and ●=butyric acid).

The fermentation broth was subjected to pervaporation studies. FIG. 6 shows total flux and selectivities of all the components of ABE fermentation products and Table 2 shows their feed and pervaporate concentration. Most interestingly, the selectivity of butanol fluctuated between 20 and 33. Selectivity of acetone varied between 15 to 22. Selectivity of butyric acid dropped from 31.5 initially to 12 during 480 minutes of operation of the membrane. Ethanol selectivity was 3.5 and acetic acid selectivity was 0.5 - 1.0. Table 2 shows ABE concentrations in feed and in pervaporate.

and selectivity of butanol. te Hennepe et al., *J. Memb. Sci.* 35 (1987) 39–55, supra, used a normalized formula to calculate flux through a thin membrane. Membranes of different thicknesses were made and the flux and selectivity of butanol were determined. For this purpose, butanol solution at a concentration of 10 g/L was made and pervaporation studies were carried out. As the thickness of a membrane decreased, flux increased sharply. With decrease in membrane thickness, selectivity decreased slightly. These studies were conducted at 35° C. and are shown in FIG. 8.

The following Example illustrates making the silicalite for use in the composite membrane of the present invention.

TABLE 2

Removal of acetone, butanol, ethanol, acetic acid, and butyric acid from ABE fermentation using a silicone membrane.

| Time min | Butanol | | Acetone | | Ethanol | | Acetic Acid | | Butyric Acid | |
|---|---|---|---|---|---|---|---|---|---|---|
| | g/L Fd | g/L Per | g/L Fd | g/L Per | g/L Fd | g/L Per | g/L Fd | g/L Per | g/L Fd | g/L Per |
| 0 | 5.57 | | 2.19 | | 0.35 | | 1.14 | | 0.92 | |
| 120 | 5.51 | 151.8 | 2.17 | 31.65 | 0.40 | 1.45 | 1.18 | 1.13 | 0.94 | 28.43 |
| 240 | 5.30 | 90–130 | 1.98 | 23.74 | 0.38 | 1.01 | 1.11 | 0.76 | 1.04 | 20.20 |
| 360 | 5.20 | 96–137 | 1.95 | 25.26 | 0.38 | 1.06 | 1.12 | 0.00 | 0.96 | 7.75 |
| 480 | 5.06 | 133 | 1.90 | 24.65 | 0.35 | 0.70 | 1.10 | 1.05 | 0.93 | 10.73 |

Fd = Feed concentration; Per = Permeate concentration.

EFFECT OF TEMPERATURE ON FLUX AND SELECTIVITY USING SILICONE MEMBRANE

Temperature is the most important factor which affects flux through the membrane. To study this, 10 g/L butanol model solution was made in distilled water and it was circulated through the membrane at various temperatures. The temperatures of study were 35, 50, 65, and 80° C. The results of this study are plotted in FIG. 7. At 35° C. the selectivity of butanol was 30. As the temperature increased to 80° C. selectivity of butanol rose to 44.9. As expected butanol flux increased linearly from 12.5 g/m²h at 35° C. to 74 g/m²h at 80° C. Table 3 shows butanol concentration in feed and in pervaporate at various temperatures.

TABLE 3

Removal of butanol from model solution at various temperatures using a silicone membrane.

| Temp. (°C.) | Time (min) | Butanol concentration (g/L) | |
|---|---|---|---|
| | | Feed | Pervaporate |
| 35 | 0 | 8.28 | |
| | 120 | 8.06 | 193.40 |
| | 240 | 8.02 | 189.10 |
| | 360 | 7.98 | 203.21 |
| 50 | 0 | 8.64 | |
| | 60 | 8.47 | 222.07 |
| | 120 | 8.24 | 211.92 |
| | 180 | 7.95 | 195.57 |
| 65 | 0 | 8.28 | |
| | 60 | 7.64 | 260.5 |
| | 120 | 6.88 | 249.22 |
| | 180 | 6.51 | 209.00 |
| 80 | 0 | 9.19 | |
| | 60 | 7.57 | 293.9 |
| | 120 | 6.89 | 246.43 |
| | 180 | 6.13 | 204.25 |

EFFECT OF MEMBRANE THICKNESS ON FLUX AND SELECTIVITY USING SILICONE MEMBRANE

Membrane thickness is one of the most important properties in pervaporation. Membrane thickness can affect flux

EXAMPLE 3

SILICALITE SYNTHESIS

Silicalite was prepared by a modified method of Grose et al., U.S. Pat. No. 4,061,724, herein incorporated by reference in its entirety. When the method of Grose et al. was employed, the resulting silicalite did not adsorb butanol at all. Thus, the procedure was modified as follows. 5 g of Aerosil 130 (Degussa Corp., Akron, Ohio) was mixed with 23 ml of deionized water in teflon beaker. This turned into a thick paste that was difficult to mix. A solution containing 0.68 g tetrapropylammonium bromide (TPABr) in 1.5 ml deionized water was added to the paste with mixing. Further, a solution containing 0.64 g NaOH in 1.5 ml deionized water was added to the paste with mixing. After thorough mixing, the beaker was placed in an air tight pressure bomb. The pressure bomb was kept at 100–110° C. for 3–5 days for the reaction to carry out. During reaction, the pressure increased inside the pressure vessel. After 3–5 days, the pressure bomb was removed from the oven and cooled to room temperature. The pressure vessel was opened when the inside pressure was reduced to atmospheric. The reaction solids were removed by centrifugation at 7000 rpm for 15 minutes in plastic centrifuge bottles on a Beckman model J2–21 centrifuge. The recovered product was washed several times with deionized water to remove any unreacted NaOH. The washed product was calcined at 600° C. for several hours in an air purge furnace.

SILICALITE BUTANOL ADSORPTION

The silicalite thus obtained was checked for butanol adsorption using acetone butanol ethanol (ABE) model solution of the following composition: acetone 2.8 g/L, butanol 10.0 g/L, ethanol 0.81 g/L, acetic acid 1.0 g/L, and butyric acid 1.0 g/L. 5 ml of the model solution was added to 1 g of silicalite and mixed for 60–120 seconds. The suspension was centrifuged in a micro centrifuge (Eppendorf centrifuge 5415C) at 14,000 rpm for 2 minutes. The clear liquid was removed and injected into GC for ABE determination. The composition was found to be: acetone 0.54 g/L, butanol 0.38 g/L, ethanol 0.63 g/L, acetic acid 0.95 g/L, and butyric acid 0.95 g/L.

SILICALITE CHARACTERIZATION

The silicalite produced in Example 2 was subjected to analyses and characterization. It was subjected to electron micrograph studies, chemical analysis, and butanol adsorption-desorption studies. Attempts were made to solubilize silicalite in several strong solvent, however, it did not dissolve.

Electron micrograph studies were done to measure the size and shape of silicalite particles. The size of the silicalite particles was found to be 3 μm and the particles were orthorhombic to spherical in shape, which is different than that reported by te Hennepe et al., *J. Memb. Sci.* 35 (1987) 39–55, supra.

The chemical composition was as follows: carbon 3.87%, hydrogen<0.5%, nitrogen<0.5%, moisture 2.21%, sodium oxide 0.647%, aluminum oxide 0.389%, and silicon dioxide 94.02%.

Acetone, butanol, ethanol, acetic acid, and butyric acid adsorption-desorption and kinetic studied were done. Adsorption studies at higher temperature were carried out in a temperature controlled water bath.

The surface area and pore diameter were 285 m$^2$/g and 10 Å, respectively.

The following Example is illustrative of making the silicalite containing membrane according to the present invention.

EXAMPLE 4

SILICALITE MEMBRANE MAKING

To make the silicalite membrane according to the present invention, 8 g RTV 615A and 0.8 g RTV 615B were mixed. 15 ml of iso-octane were added and thoroughly mixed as detailed above in Example 2. 5.6 g of silicalite as prepared by the method of Example 3 were added and mixed thoroughly. This suspension was poured onto a Teflon plate and spread mechanically to form a uniform liquid thickness. The plate was placed in an oven for 10–20 hours. Once the membrane was cured, it was peeled off the plate and cut to the size of the pervaporation plate. Membranes with various silicalite contents were made and characterized for butanol selectivity and flux. The thickness of the membranes ranged from 96–434 μm.

The following Example illustrates the ABE fermentation method.

EXAMPLE 5

ABE PRODUCTION USING CELLS OF *CLOSTRIDIUM ACETOBUTYLICUM*

Whenever necessary, ABE were produced in a 2 L New Brunswick fermentor using *Clostridium acetobutylicum* ATCC 824 and a medium given by Ennis et al., *Biotechnol. Lett.* 7 (1985) 601–606, supra. *Clostridium acetobutylicum* ATCC 824 was obtained from American Type Culture Collection and maintained as spores in distilled water. Glucose was used as a substrate. Cysteine HCl·H$_2$O was filter sterilized through a 0.45 μm size filter, while the rest of the medium was autoclaved at 121° C. for 15 min. Spores of the culture were heat shocked in 25 mL screw capped test tubes for 2–3 minutes in cooked meat medium and glucose, followed by cooling in ice cold water for one minute as described by Ennis et al., *Biotechnol. Lett.* 7 (1985) 601–606, supra. These tubes were then incubated at 35° C. for 18–20 hours in an anaerobic chamber. Further, inoculum was developed in 100 mL screw capped bottles containing the above liquid medium and 30 g/L glucose. These bottles were inoculated with 2–5 mL inoculum developed above and incubated for 18–20 hours at 35° C. in an anaerobic chamber. The ABE production reactor was inoculated with the inoculum developed in bottles at the level of 5–10% (v/v) (of the final volume in ABE production reactor). The pH was controlled at 5.0 in the fermentor. Fermentation took about 3 days before it was complete. At the end of fermentation, total solvents were at about 8.5 g/L and cells were at 3 g/L. The fermentation broth was circulated through the membrane without removing cells.

The following Example illustrates the method of measuring acetone, butanol, ethanol, acetic acid, and butyric acid.

EXAMPLE 6

GAS CHROMATOGRAPH ANALYSES

Acetone, butanol, ethanol, acetic acid, and butyric acid were measured using a gas chromatograph (Hewlett Packard, Avondale, Pa.). The gas chromatograph was equipped with a Flame Ionization Detector and an integrator. The glass column (1837×2 mm) (Supelco Inc.) was packed with carbowax 20M (Carbowax 20M Terephthalic acid 10%, phosphoric acid 85%, and 0.01% chromosorb WAW 80/100). The carrier gas (nitrogen) flow rate was 30 mL/min. Details of the column conditions are given above in Table 1. Samples containing cells or any dirt material were centrifuged at 14000 rpm in a micro centrifuge.

In most cases the pervaporated condensate had separated into two phases: the aqueous phase (bottom layer containing butanol at 78 g/L) and organic phase. To measure the concentration of butanol in the condensate, both of these phases were diluted together by adding a known amount of water until a single phase appeared. Before injecting into the GC, the butanol concentration was diluted to less than 10 g/L. Glucose in the fermentation broth and fermentation medium was measured by an enzymatic method (Glucose Oxidase, YSI Model 27), and cells were measured by an optical density method.

EXAMPLE 7

ADSORPTION OF ABE FERMENTATION PRODUCTS USING SILICALITE

Silicalite was made in batches to adsorb desired ABE fermentation products. These fermentation products include acetone, butanol, and ethanol. Adsorption of reaction intermediates is not desired. To study adsorption of ABE, the silicalite was made as described above in Example 3.

5 g of Aerosil 130 were mixed with 23 ml of deionized water. To this mixture, a solution of 0.68 g tetrapropylammonium bromide in 1.5 ml deionized water was added with stirring. Then a solution of 0.64 g NaOH in 1.5 ml deionized water was added. The mixture was kept in a pressure bomb at 100°–110° C. as detailed above. After calcination, adsorption of silicalite was checked. 1 g of silicalite was added to 5 ml ABE solution and concentrations of ABE fermentation products were determined before and after the adsorption. The results are shown in Table 4.

TABLE 4

ABE fermentation product concentrations before and after adsorption on silicalite.

| ABE | Before adsorption (g/L) | After adsorption (g/L) |
| --- | --- | --- |
| Acetone | 2.84 | 0.31 |
| Butanol | 10.21 | 0.12 |
| Ethanol | 1.00 | 0.50 |
| Acetic Acid | 1.10 | 1.00 |
| Butyric Acid | 1.10 | 1.00 |

EXAMPLE 8

Example 7 was repeated except that 10 g of aerosil 130 in 46.6 ml water, 1.36 g TPABr in 2.5 ml water, and 1.28 g NaOH in 2.5 ml water were used. After calcination, the silicalite was checked for ABE adsorption and the results are shown in Table 5.

TABLE 5

ABE fermentation product concentrations before and after adsorption on silicalite.

| ABE | Before adsorption g/L | After adsorption g/L |
| --- | --- | --- |
| Acetone | 2.86 | 0.40 |
| Butanol | 10.17 | 0.21 |
| Ethanol | 1.01 | 0.52 |
| Acetic Acid | 1.00 | 0.94 |
| Butyric Acid | 1.03 | 1.09 |

EXAMPLE 9

Example 7 was repeated except that 20 g of aerosil 130 in 93 ml water; 2.72 g TPABr in 5 ml water; and 2.56 g NaOH in 5 ml water were used. The silicalite was checked for ABE adsorption and the results are shown in Table 6.

TABLE 6

ABE fermentation product concentrations before and after adsorption on silicalite.

| ABE | Before adsorption (g/L) | After adsorption (g/L) |
| --- | --- | --- |
| Acetone | 2.83 | 0.13 |
| Butanol | 10.00 | 0.00 |
| Ethanol | 1.03 | 0.41 |
| Acetic Acid | 1.03 | 1.04 |
| Butyric Acid | 1.10 | 1.05 |

The above Examples 6–9 for adsorbing ABE fermentation products demonstrate the reproducibility of the process of making silicalite of the present invention and the high degree of selectivity of the silicalite according to the present invention. Acetone, butanol, and ethanol were adsorbed by the silicalite, while acetic acid and butyric acid were not.

EXAMPLE 10

ABE ADSORPTION KINETICS

To study the kinetics of ABE adsorption, an ABE solution containing acetone 2.8 g/L, butanol 10 g/L, ethanol 1.01 g/L, acetic acid 1.03 g/L, and butyric acid 1.00 g/L was taken. 3 g silicalite was added to 15 ml of the above solution and samples were taken at different time intervals. The first sample was taken after 30 seconds. The samples were then centrifuged to remove silicalite particles and the supernatents were injected into GC for analysis. These studies were conducted at 25°–27° C. The concentrations of residual ABE after adsorption are shown in Table 7. Clearly, acetone, ethanol, and butanol were adsorbed within less than 30 seconds. Possibly the adsorption is instantaneous. Acetic acid and butyric acid are not adsorbed, even on prolonged contact.

TABLE 7

Adsorption kinetics of ABE onto silicalite.

| | Concentration (g/L) | | | | |
| --- | --- | --- | --- | --- | --- |
| Time | Acetone | Butanol | Ethanol | Acetic Acid | Butyric Acid |
| 0 sec | 2.8 | 10 | 1.01 | 1.03 | 1.00 |
| 30 sec | 0.12 | 0.00 | 0.46 | 1.17 | 1.13 |
| 60 sec | 0.14 | 0.00 | 0.36 | 0.92 | 0.92 |
| 90 sec | 0.11 | 0.00 | 0.35 | 0.98 | 1.00 |
| 120 sec | 0.12 | 0.00 | 0.32 | 1.10 | 1.05 |
| 30 min | 0.13 | 0.00 | 0.34 | 0.97 | 0.96 |

EXAMPLE 11

ADSORPTION CAPACITIES FOR DIFFERENT ABE COMPONENTS

To determine the adsorption capacities for different ABE components, an ABE solution having the following formulation was prepared: acetone 2.61 g/L, butanol 9.7 g/L, ethanol 0.94 g/L, acetic acid 1.03 g/L, and butyric acid 1.06 g/L. Various amounts of this solution were added to 0.32 to 0.25 g silicalite as shown in Table 8. Enough time was allowed for the adsorption to reach the maximum limit (about 30 minutes). Samples were then taken to analyze the residual ABE. The concentrations of ABE after adsorption and the adsorbed amounts are given in Table 8. Acetone 8–12 mg/g, butanol 85–90 mg/g, ethanol 1–2 mg/g, acetic acid about 1 mg/g, and butyric acid 2–6 mg/g were adsorbed. Table 8 shows that at the end of the adsorption, significant amounts of these residual components remained in the solution. The above adsorbed amounts are the maximum limits the silicalite can adsorb.

TABLE 8

| Amount of silicalite | ml ABE solution | Products after adsorption (g/L) | | | | | Adsorbed products (mg/g) | | | | |
| --- | --- | --- | --- | --- | --- | --- | --- | --- | --- | --- | --- |
| | | AC$_2$O | BuOH | EtOH | HAc | HBu | AC$_2$O | BuOH | EtOH | HAc | HBu |
| 0.32 g | 1.60 | 0.17 | 0.00 | 0.43 | 1.00 | 1.01 | 12.20 | 48.50 | 2.55 | 0.15 | 0.25 |
| 0.25 g | 1.88 | 1.52 | 1.48 | 0.80 | 1.03 | 1.03 | 8.20 | 61.81 | 1.06 | 0.00 | 0.23 |

TABLE 8-continued

| Amount of silicalite | ml ABE solution | Products after adsorption (g/L) | | | | | Adsorbed products (mg/g) | | | | |
|---|---|---|---|---|---|---|---|---|---|---|---|
| | | $AC_2O$ | BuOH | EtOH | HAc | HBu | $AC_2O$ | BuOH | EtOH | HAc | HBu |
| 0.25 g | 2.50 | 1.83 | 2.81 | 0.82 | 0.98 | 1.00 | 7.80 | 68.90 | 1.20 | 0.50 | 0.60 |
| 0.25 g | 3.13 | 2.01 | 3.70 | 0.85 | 1.00 | 0.98 | 7.51 | 75.12 | 1.13 | 0.38 | 1.00 |
| 0.25 g | 3.75 | 2.15 | 3.97 | 0.89 | 1.01 | 0.93 | 6.90 | 85.95 | 0.45 | 0.30 | 1.95 |
| 0.25 g | 4.38 | 2.20 | 4.58 | 0.88 | 0.97 | 0.82 | 7.70 | 89.70 | 0.70 | 1.05 | 4.20 |
| 0.25 g | 5.00 | 2.29 | 5.41 | 0.90 | 0.97 | 0.75 | 6.40 | 85.80 | 0.40 | 1.20 | 6.20 |

$AC_2O$ = acetone, BuOH = butanol, EtOH = ethanol, HAc = acetic acid, HBu = butyric acid.

The following Example illustrates the flux and selectivity characteristics of ABE upon the repeated use of silicalite.

EXAMPLE 12

REPEATED USE OF SILICALITE

ABE was adsorbed onto silicalite as detailed above using an ABE solution containing acetone 2.84 g/L, butanol 10.20 g/L, ethanol 1.00 g/L, acetic acid 1.09 g/L, and butyric acid 1.10 g/L. The silicalite was then desorbed at 80° C. for 12–15 hours. 5 ml of the above ABE solution was then added to 1 g of desorbed silicalite for readsorption. After readsorption, samples were taken to check if the silicalite readsorbed ABE. The concentrations of ABE components in the supernatant were acetone 0.19 g/L, butanol 0.00 g/L, ethanol 0.45 g/L, acetic acid 1.27 g/L, and butyric acid 0.26 g/L. The desorbed silicalite readsorbed acetone, butanol, and ethanol as does the fresh silicalite. In addition, it adsorbed butyric acid. At this stage, it is not known why it adsorbed butyric acid. Possibly, butyric acid interacted with the silicalite during the desorption process at high temperature.

EXAMPLE 13

EFFECT OF TEMPERATURE ON DESORPTION

Further desorption studies of ABE were conducted under vacuum and at different temperatures (36° C., 65° C., and 78° C.). The desorption was conducted in a vacuum jar. 2 to 3 g of silicalite were treated with 15 ml of ABE solution of the composition given in Table 9. The sample was placed in the vacuum jar and kept at the desired temperature (36° C. to 78° C.) in a water bath. The jar was connected to a cooling finger using stainless steel vacuum tubing. The cooling finger was connected to a vacuum pump. These studies were conducted for 1 to 1.5 hours at each temperature and the adsorbed amounts of ABE were calculated. The values of adsorbed and desorbed ABE components are given in Table 9. It shows that at 78° C., the desorption of ABE is faster and thus would be an appropriate temperature to desorb ABE from the membrane.

TABLE 9

Desorption of ABE from silicalite under vacuum at different temperatures.

| | Before adsorption (g/L) | After adsorption (g/L) | Adsorbed amount | Desorbed amount |
|---|---|---|---|---|
| Desorption at 36° C. | | | | |
| Acetone | 2.33 | 0.13 | 0.033 | 0.015 |
| Butanol | 8.95 | 0.00 | 0.134 | 0.072 |
| Ethanol | 0.89 | 0.39 | 0.008 | 0.005 |

TABLE 9-continued

Desorption of ABE from silicalite under vacuum at different temperatures.

| | Before adsorption (g/L) | After adsorption (g/L) | Adsorbed amount | Desorbed amount |
|---|---|---|---|---|
| Acetic acid | 0.97 | 1.01 | 0.000 | 0.005 |
| Butyric acid | 0.99 | 0.99 | 0.000 | 0.000 |
| Desorption at 65° C. | | | | |
| Acetone | 2.45 | 0.17 | 0.023 | 0.019 |
| Butanol | 9.91 | 0.58 | 0.093 | 0.085 |
| Ethanol | 0.98 | 0.43 | 0.006 | 0.004 |
| Acetic acid | 1.02 | 1.03 | 0.000 | 0.000 |
| Butyric acid | 1.06 | 1.04 | 0.000 | 0.000 |
| Desorption at 78° C. | | | | |
| Acetone | 3.39 | 1.18 | 0.022 | 0.021 |
| Butanol | 10.83 | 1.79 | 0.090 | 0.090 |
| Ethanol | 1.03 | 0.86 | 0.002 | 0.016 |
| Acetic acid | 1.05 | 1.01 | 0.000 | 0.000 |
| Butyric acid | 1.08 | 1.03 | 0.000 | 0.000 |

Adsorption studies at 78° C. were also conducted. 5 ml of ABE solution containing acetone 2.33 g/L, butanol 9.00 g/L, ethanol 0.9 g/L, acetic acid 1.01 g/L, and butyric acid 1.00 g/L were added to 1 g of silicalite in a sealed test tube kept at 78° C. After 30 seconds, a sample was taken and the concentration of ABE was measured. The concentrations of acetone, butanol, ethanol, acetic acid, and butyric acid were 0.13, 0.00, 0.38, 0.92, and 0.77 g/L, respectively. This clearly shows that adsorption occurs a 78° C. with the same capacity and efficiency.

EXAMPLE 14

SILICALITE MEMBRANE

Figure 9:
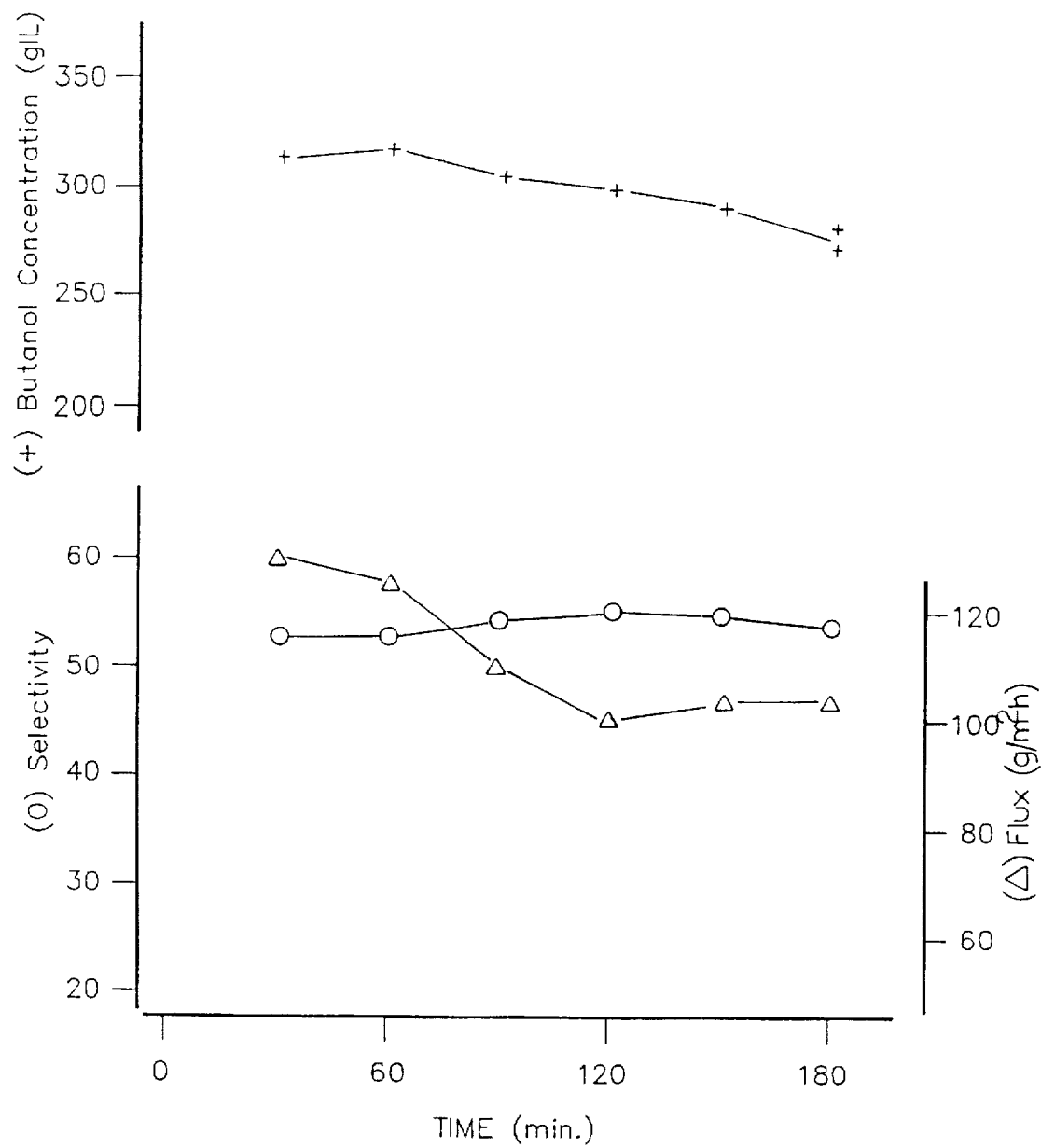
FIG. 9 shows butanol selectivity of a membrane loaded at a silicalite:polymer ratio of 0.64 by weight (wherein ○=selectivity, △=flux, and +=pervaporate butanol concentration).

A silicalite membrane was made with a silicalite to total polymer (including initiator) ratio of 0.64 by weight (5.6/8.8). After curing, the membrane was used in the pervaporation machine to determine selectivity and flux using model solution. The operational temperature of the membrane was selected to be 78° C. due to faster desorption of butanol at that temperature. The selectivity of the membrane varied between 53 and 55.37. The results are shown in FIG. 9. The machine operated for 3 hours after the steady state had been reached. The total flux in the beginning of the experiment was 130 g/m²h which dropped to 105 g/m²h. The concentration of butanol decreases with time. The concentration of butanol in the permeate reached a value of 308.5 g/L. At that time, the average concentration of butanol in the feed was 8.36 g/L. At this temperature, butanol selectivity of silicone membrane was 44.44, and the total flux varied between 80.14 g/m²h and 65.9 g/m²h. A comparison of the results from the two membranes shows that the silicalite membrane performed better than the silicone membrane, both in terms of flux and selectivity. The loading of silicalite was low in this case. The studies on the silicalite content of the membrane are reported below.

Studies were done on the inclusion of higher amounts of silicalite in the membrane. The various ratios of silicalite:polymer used to load the membrane were 1, 1.5, 2.12, and 2.5, by weight. The results of these membranes are given in FIG. 10. As the loading of silicalite increased, so did the selectivity and butanol concentration in the permeate. At these ratios, the selectivities of butanol were 70.0, 100.5, 108.7–120, and 135–141, respectively. Total flux initially increased to 122.6 g/m²h, and then decreased to 80 g/m²h due to increased membrane thickness at higher loading of silicalite. A membrane with silicalite loading ratio of 2.5 by weight resulted in a butanol concentration of over 490 g/L on the permeate side when the butanol concentration in the retentate was 6.87 g/L.

EXAMPLE 15

TEMPERATURE OPTIMIZATION

A membrane with silicalite loading of 1.5 was selected for these studies. The thickness of the membrane was 306 μm. Butanol solution of about 10 g/L was used for these studies. The temperatures at which the membrane was operated were 35, 45, 55, 65, 78, and 85° C. A plot of temperature vs. flux and selectivity is shown in FIG. 11. At temperatures below 65° C., selectivities fluctuated as shown in FIG. 11. As expected, the flux increased with the temperature. Above 85° C., the pump started pumping vapors, not liquid.

EXAMPLE 16

EFFECT OF FERMENTATION MEDIUM ON FLUX AND SELECTIVITY

Figure 12:
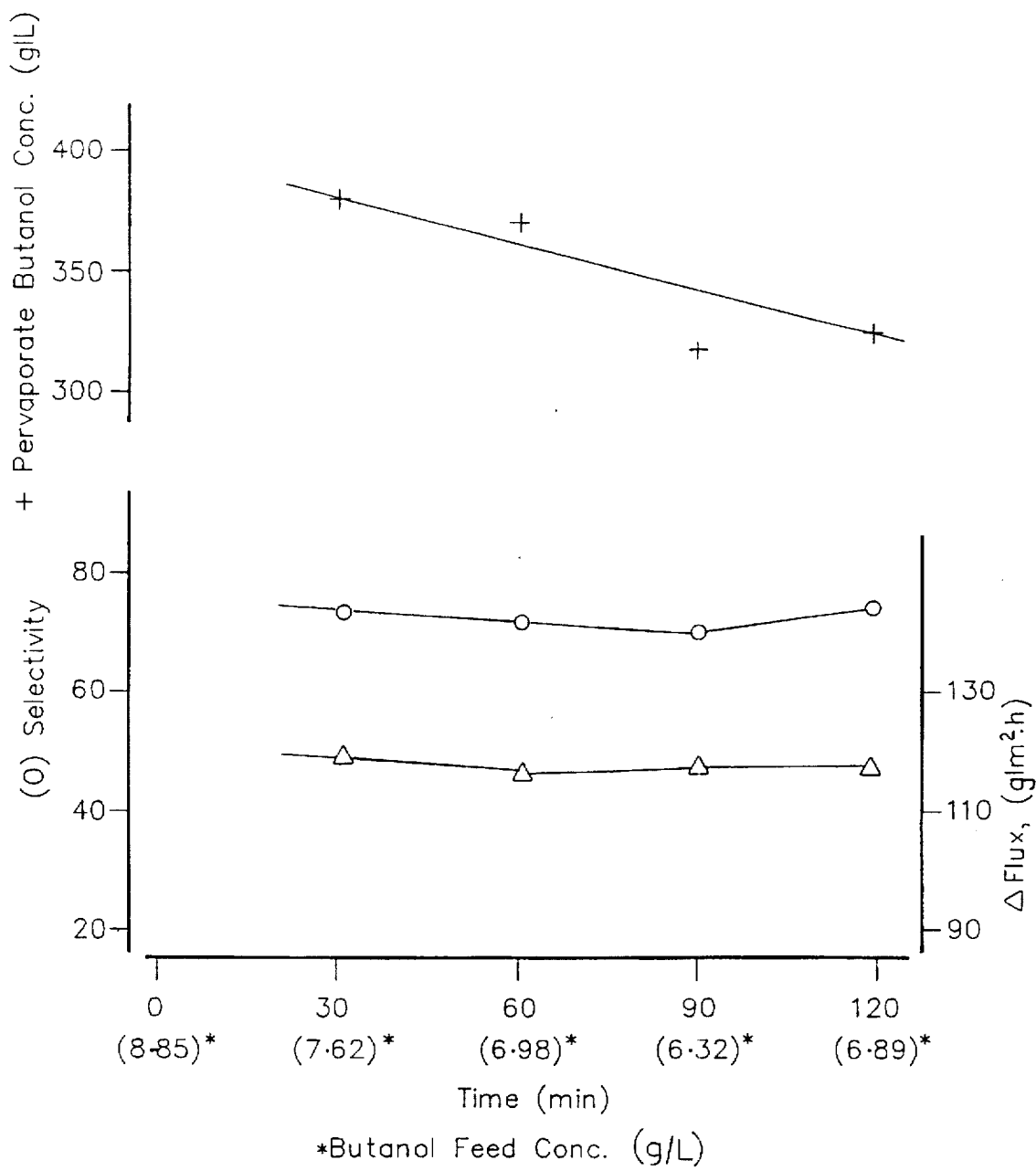
FIG. 12 shows the removal of butanol from fermentation medium by pervaporation using a silicalite membrane with Ws:Wp=1.0 (wherein ○=selectivity, Δ=flux, and +=pervaporate butanol concentration).

A silicalite membrane (silicalite:polymer=1.0 by weight) was used to determine whether butanol flux and selectivity are affected by fermentation medium. The composition of the fermentation medium is described above in Example 5. Butanol solution was initially taken at 10 g/L. The experiment was operated under steady state for 120 minutes and is shown in FIG. 12. The selectivity of the membrane was 70–72 and the flux was from 120–116 g/m²h. Results show that the membrane was not fouled by the fermentation medium in view of the fact that the flux and selectivity of this membrane with the model solution were 70 and 122 g/m²h, respectively. Butanol concentration in the permeate ranged from 370 to 325 g/L when butanol in the feed tank was 7.62 to 6.09 g/L, respectively.

EXAMPLE 17

EFFECT OF FERMENTATION BROTH ON FLUX AND SELECTIVITY

Figure 13:
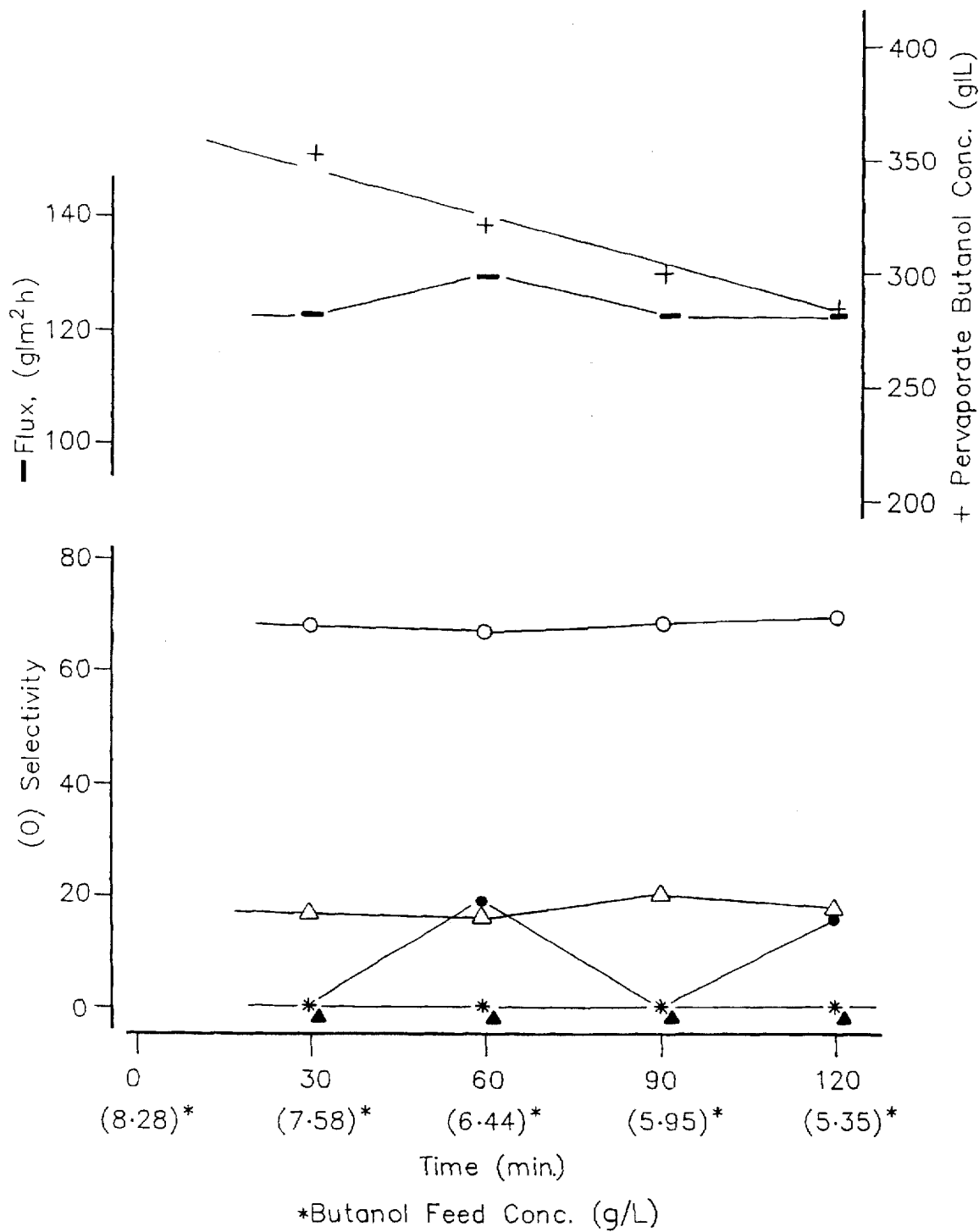
FIG. 13 shows ABE removal from fermentation broth of *Clostridium acetobutylicum* ATCC 824 by pervaporation using a silicalite membrane with Ws:Wp=1 (wherein Δ=acetone, ○=butanol, *=ethanol, ▲=acetic acid, ●=butyric acid, —=flux, and +=pervaporate butanol concentration).

Since the fermentation medium did not foul the membrane, whether the fermentation broth will foul it was investigated. The results of this investigation are given in FIG. 13. The total flux was 121 g/m²h and butanol selectivity was 69–70. Acetone selectivity was 18 to 40. Ethanol and acetic acid selectivities were zero. Table 10 shows concentrations of ethanol, acetone, acetic acid, and butyric acid in feed and pervaporate.

TABLE 10

Removal of acetone, ethanol, acetic acid, and butyric acid from fermentation broth using silicalite membrane (Ws/Wp = 1.0).

| Time (min) | Concentration (g/L) | | | | | | | |
|---|---|---|---|---|---|---|---|---|
| | Acetone | | Ethanol | | Acetic acid | | Butyric acid | |
| | Fd | Per | Fd | Per | Fd | Per | Fd | Per |
| 0 | 2.11 | | 0.28 | | 1.07 | | 0.89 | |
| 30 | 2.05 | 76.95 | 0.26 | 0.00 | 1.15 | 0.00 | 0.93 | 0.00 |
| 60 | 1.79 | 64.18 | 0.30 | 0.00 | 1.04 | 0.00 | 1.04 | 16.81 |
| 90 | 1.67 | 60.30 | 0.30 | 0.00 | 1.05 | 0.00 | 0.94 | 0.00 |
| 120 | 1.60 | 28.70 | 0.33 | 0.00 | 1.02 | 0.00 | 0.78 | 13.00 |

Fd = Feed concentration; Per = Permeate concentration.

After the above two experiments, the membrane was checked for its flux and selectivity using model butanol solution. The flux and selectivity using this membrane were 120–122 g/m²h and 70, respectively. The membrane was operated for 90 minutes under steady state conditions. These experiments demonstrate that the membrane is not fouled either by fermentation medium or fermentation broth. It should be noted that the cells were not removed from the fermentation broth.

EXAMPLE 18

EFFECT OF MEMBRANE THICKNESS ON SELECTIVITY AND FLUX

Membrane thickness is an industrially important property. The thickness of a membrane can affect flux and selectivity. To study this factor different thickness membranes were made with silicalite loading of 1.5 (Ws/Wp). These membranes were 96, 125, 200, and 306 μm thick. Each of these membranes were characterized for flux and selectivity using 10 g/L butanol model solution (FIG. 14). The operation temperature for these studies was 78° C. As the silicalite membrane thickness increased selectivity of butanol increased. A thin membrane (96 μm) gave a selectivity of 50 and a thick (306 μm) membrane gave a selectivity of 100–108. This suggests that to achieve a high selectivity a silicalite membrane needs to be thick. While not wishing to be bound by a particular theory, it is believed that the added layers of silicalite help enrich butanol through the membrane. As expected, a thin membrane results in higher flux. A 96 μm thick membrane showed a flux of 235 g/m²h (and a selectivity of 50) and a 306 μm thick membrane showered a flux of 85–90 g/m²h (and a selectivity of 100–108). It can be concluded from these studies that for a silicalite membrane, a compromise needs to be made between flux and selectivity keeping membrane thickness in view.

EXAMPLE 19

Butanol above 78 g/L separates into two phases; the top organic phase which possibly contains butanol at 810 g/L and the bottom aqueous phase which contains butanol at 78 g/L. The top organic phase may not need further treatment and may be used for fuel purposes. The aqueous phase may be recycled to the membrane to remove butanol from it. We ran experiments to separate butanol from 75 g/L butanol solution using a silicalite membrane with silicalite to polymer ratio of 1.5 (Ws/Wp). The selectivities and flux values for this separation are plotted in FIG. 15. At lower concentration of butanol in the retentate, butanol selectivity was high. At retentate butanol of 5 g/L, selectivity of butanol was 94–106 and flux was about 85–90 g/m²h. At retentate butanol of 1.62 g/L, butanol selectivity of 160.84 was achieved. This gave a flux of 70.45 g/m²h. Further decrease of retentate butanol to 1.32 g/L resulted in a butanol selectivity of 196.77 and flux of 68.64 g/m²h. Further attempts were made to decrease retentate butanol concentration below 1 g/L. At 0.93 g/L retentate butanol a maximum selectivity of 209.10 was achieved with a flux of 67.27 g/m²h. Further decrease in retentate butanol concentration resulted in lower selectivities. At concentration of 0.37 g/L butanol selectivity of 178.63 was achieved. At lower concentrations of butanol, total flux was low. As retentate butanol concentration increased towards 75 g/L selectivity decreased and flux increased. At a butanol concentration of 60 g/L a selectivity of 66 and flux of 190 g/m²h was obtained. The results indicate that the membrane of the present invention gives good results for all concentrations of butanol, whether high or low. However, it is not understood why high selectivities were achieved at low concentrations of butanol.

EXAMPLE 20

Attempts were made to separate acetone, ethanol, acetic acid and butyric acid from their mixture using a silicalite membrane (Ws/Wp 1.0) at 78° C. Their concentrations in the retentate mixture and in the permeate are shown in Table 11.

TABLE 11

Flux and selectivity of acetone, ethanol, acetic acid and butyric acid through a silicalite membrane.

| | Time (hours) | | | | |
|---|---|---|---|---|---|
| | 0 | 1 | 2 | 3 | 4 |
| Acetone | | | | | |
| Feed (g/L) | 3.35 | 2.93 | 2.58 | 2.45 | 2.10 |
| Permeate (g/L) | — | 112.91 | 112.65 | 98.30 | 95.80 |
| Selectivity (–) | — | 40.41 | 45.95 | 43.09 | 46.46 |
| Flux (g/m²h) | — | 94.55 | 97.73 | 86.18 | 83.18 |
| Ethanol | | | | | |
| Feed(g/L) | 1.13 | 1.08 | 1.02 | 1.07 | 1.00 |
| Permeate (g/L) | — | 4.40 | 7.43 | 4.57 | 0.00 |
| Selectivity (–) | — | 4.01 | 7.12 | 4.38 | 0.00 |
| Flux (g/m²h) | — | * | * | * | * |
| Acetic acid | | | | | |
| Feed (g/L) | 0.97 | 0.88 | 0.90 | 0.91 | 0.85 |
| Permeate (g/L) | — | 0.00 | 0.00 | 0.00 | 0.00 |
| Selectivity (–) | — | 0.00 | 0.00 | 0.00 | 0.00 |
| Flux (g/m²h) | — | * | * | * | * |
| Butyric acid | | | | | |
| Feed (g/L) | 1.01 | 0.83 | 0.82 | 0.79 | 0.79 |
| Permeate (g/L) | — | 8.87 | 6.53 | 7.11 | 9.29 |
| Selectivity (–) | — | 9.72 | 8.00 | 8.89 | 12.49 |
| Flux (g/m²h) | — | * | * | * | * |

* Flux same as for acetone.

Selectivity of acetone at 3.14 to 2.28 g/L retentate concentration was 40.41 to 46.46. Experiments run with fermentation broth showed acetone selectivities of 18 to 40 (Example 17). At ethanol concentration of 1 g/L ethanol selectivity of 4.01 to 7.12 was obtained. Acetic acid did not diffuse through the membrane at a retentate concentration of 0.93. Interestingly, selectivity of butyric acid was found to be 8.00 to 12.49. Flux through the membrane was 83.18 g/m²h to 94.55 g/m²h. Results indicate that this membrane has enhanced selectivity for acetone compared to silicone membrane. Silicone membrane gave an acetone selectivity of 9.35–20.38 at retentate acetone of 0.38–2.35 g/L. With a silicone membrane, ethanol selectivity of 5.65–7.61 was obtained at ethanol concentration of 0.98 to 0.25 g/L.

Higher retentate concentration of ethanol was also attempted in this membrane. At an ethanol concentration of 79.27–80.74 g/L, ethanol selectivity of 1.08–1.39 was obtained. The results are given in Table 12.

TABLE 12

Flux and selectivity of ethanol using a silicalite membrane (membrane thickness 226 μm).

| Time (hours) | Feed ethanol concentration (g/L) | Pervaporate ethanol concentration (g/L) | Ethanol selectivity | Total flux (g/m²h) |
|---|---|---|---|---|
| 1 | 80.74 | 108.93 | 1.39 | 14.55 |
| 2 | 79.73 | 90.18 | 1.17 | 20.90 |
| 3 | 79.58 | 93.29 | 1.19 | 16.59 |
| 4 | 79.27 | 85.07 | 1.08 | 17.06 |

The total flux was 14.55–17.06 g/m²h. Inclusion of silicalite into the membrane did not affect ethanol and acetic acid selectivities. Butyric acid selectivity appears to have increased with the inclusion of silicalite.

In a preferred embodiment of the present invention, the silicalite membrane comprises a silicone membrane that is from about 25 μm to about 450 μm thick, with a membrane thickness of from about 300 μm to about 434 μm being particularly preferred. A membrane loading of from about 0.5 g to about 2.5 g silicalite per 1 g polymer may be used, with about 1.5 g to about 2.5 g silicalite per 1 g polymer being especially preferred. The polymer used is preferably a silicone polymer or cellulose acetate, with polydimethylsiloxane being especially preferred. The preferred operational temperature is from about 35° C. to about 80° C., with a temperatutre of about 78° C. being particularly preferred.

In a particularly preferred embodiment of the present invention, the silicalite membrane comprises a silicone membrane that is 300 μm thick with a loading of 1.5 g silicalite per 1 g silicone. The optimal operational temperature is about 78° C. The resulting flux is 100 g/m²h and the selectivity is 100–200, depending on the concentration of butanol in the feed. For example, using a retentate concentration of 10 g/L of butanol, the permeate concentration is 500 g/L. With a retentate concentration of 20 g/L of butanol, the permeate concentration is 660 g/L.

All references cited herein are hereby expressly incorporated by reference in their entireties.

The description above should not be construed as limiting the scope of the invention, but as merely providing illustrations to some of the presently preferred embodiments of this invention. In light of the above description and examples, various other modifications and variations will now become apparent to those skilled in the art without departing from the spirit and scope of the present invention as defined by the appended claims. Accordingly, the scope of the invention should be determined solely by the appended claims and their legal equivalents.

What is claimed is:

1. A pervaporation process for the selective removal of acetone and/or butanol from an aqueous solution comprising acetone or butanol, or mixtures thereof, comprising the steps of (a) delivering an aqueous solution comprising acetone and/or butanol to the feed side of a pervaporation membrane having a first feed side and a second permeate side; (b) applying a driving force to cause permeation of the membrane by said aqueous solution; and (c) collecting the pervaporate exiting from said permeate side, wherein said pervaporation membrane comprises silicalite particles embedded in a polymer matrix, and wherein the adsorption of acetone and/or butanol by the membrane is substantially greater than the adsorption of ethanol.

2. The pervaporation process of claim 1 wherein butanol selectivity is from about 100 to about 200 and/or acetone selectivity is from about 18 to about 40.

3. The pervaporation process of claim 2 wherein said aqueous solution further comprises ethanol, and wherein ethanol selectivity is less than about 2.

4. The pervaporation process of claim 3 wherein said aqueous solution further comprises acetic acid and/or butyric acid and wherein acetic acid selectivity is about zero and/or butyric acid is less than about 20.

5. The pervaporation process of claim 3 wherein the silicalite:polymer weight ratio of said pervaporation membrane is from about 1.5 to about 2.5.

6. The pervaporation process of claim 5 wherein said polymer is polydimethylsiloxane.

7. The pervaporation process of claim 3 wherein the membrane thickness of said pervaporation membrane is from about 300 μm to about 434 μm.

8. The pervaporation process of claim 7 wherein said polymer is polydimethylsiloxane.

9. The pervaporation process of claim 3 wherein said polymer is cellulose acetate.

10. The pervaporation process of claim 3 wherein said silicalite particles are crystalline.

11. The pervaporation process of claim 3 wherein the size of said said silicalite particles is from about 3 μm to about 45 μm.

12. The pervaporation process of claim 3 wherein the surface area of the silicalite is about 285 m$^2$/g.

13. The pervaporation process of claim 3 wherein the pore diameter of said silicalite particles is about 10 Å.

14. The pervaporation process of claim 3 wherein said driving force is a pressure differential across the membrane.

15. The pervaporation process of claim 14 wherein said pressure differential comprises a vacuum on said permeate side of said membrane.

16. The pervaporation process of claim 15 wherein the pressure of said vacuum is from about 2 mm Hg to about 4 mm Hg.

17. The pervaporation process of claim 16 wherein the pressure on said feed side of said membrane is from about 2 to about 4 psig.

18. The pervaporation process of claim 3 wherein said aqueous solution is a model acetone butanol ethanol solution.

19. The pervaporation process of claim 3 wherein said aqueous solution is a fermentation broth.

20. The pervaporation process of claim 19 wherein the fermentation broth is produced by acetone butanol ethanol fermentation by *Clostridium acetobutylicum* and wherein the *Clostridium acetobutylicum* cells are not removed from the fermentation broth.

21. The pervaporation process of claim 3 wherein the process is performed continuously.

22. The pervaporation process of claim 3 wherein the process is performed batchwise.

23. The pervaporation process of claim 22 wherein said aqueous solution is circulated at a rate of from about 2 to about 3 L/min.

24. The pervaporation process of claim 3 wherein the process is performed batchwise.

25. The pervaporation process of claim 24 wherein said aqueous solution is circulated at a rate of from about 2 to about 3 L/min.

26. The pervaporation process of claim 3 wherein the temperature ranges from about 35° C. to about 850° C.

27. The pervaporation process of claim 26 wherein the temperature is about 78° C.

28. The pervaporation process of claim 3 wherein the permeate is collected by condensation and wherein the condensate forms an aqueous phase and an organic phase and wherein said aqueous phase is recycled to the feed stream.

29. The pervaporation process of claim 3 wherein said pervaporation membrane may be reused.

30. The pervaporation process of claim 29 wherein said pervaporaition membrane may be used for at least six months.

31. The pervaporation process of claim 30 wherein said pervaporation membrane may be used for at least one year.

32. The pervaporation process of claim 1 wherein the silicalite:polymer weight ratio of said pervaporation membrane is from about 0.5 to about 2.5.

33. The pervaporation process of claim 32 wherein the silicalite:polymer weight ratio of said pervaporation membrane is from about 1.0 to about 2.5.

34. The pervaporation process of claim 33 wherein the silicalite:polymer weight ratio of said pervaporation membrane is from about 1.5 to about 2.5.

35. The pervaporation process of claim 1 wherein the membrane thickness of said pervaporation membrane is from about 25 μm to about 450 μm.

36. The pervaporation process of claim 35 wherein the membrane thickness of said pervaporation membrane is from about 300 μm to about 434 μm.

37. The pervaporation process of claim 1 wherein said polymer matrix is a silicone polymer.

38. The pervaporation process of claim 37 wherein said polymer is polydi(lower alkyl)siloxane.

39. The pervaporation process of claim 38 wherein said polymer is polydimethylsiloxane.

40. The pervaporation process of claim 39 wherein said polymer is polydimethylsiloxane.

41. The pervaporation process of claim 1 wherein said polymer is cellulose acetate.

42. The pervaporation process of claim 1 wherein said silicalite particles are crystalline.

43. The pervaporation process of claim 1 wherein the size of said said silicalite particles is from about 3 μm to about 45 μm.

44. The pervaporation process of claim 43 wherein the size of said said silicalite particles is about 3 μm.

45. The pervaporation process of claim 1 wherein the surface area of the silicalite is about 285 m$^2$/g.

46. The pervaporation process of claim 1 wherein the pore diameter of said silicalite particles is about 10 Å.

47. The pervaporation process of claim 1 wherein said driving force is a pressure differential across the membrane.

48. The pervaporation process of claim 1 wherein said aqueous solution is a model acetone butanol ethanol solution.

49. The pervaporation process of claim 1 wherein said aqueous solution is a fermentation broth.

50. The pervaporation process of claim 49 wherein the fermentation broth is produced by acetone butanol ethanol fermentation by *Clostridium acetobutylicum*.

51. The pervaporation process of claim 50 wherein said *Clostridium acetobutylicum* is *Clostridium acetobutylicum* ATCC 824.

52. The pervaporation process of claim 50 wherein the *Clostridium acetobutylicum* cells are not removed from the fermentation broth.

53. The pervaporation process of claim 50 wherein the *Clostridium acetobutylicum* cells are not removed from the fermentation broth.

54. The pervaporation process of claim 1 wherein the process is performed continuously.

55. The pervaporation process of claim 1 wherein the process is performed batchwise.

56. The pervaporation process of claim 1 wherein the temperature ranges from about 35° C. to about 850° C.

57. The pervaporation process of claim 56 wherein the temperature is about 78° C.

58. The pervaporation process of claim 1 wherein the permeate is collected by condensation.

59. The pervaporation process of claim 58 wherein the condensate forms an aqueous phase and an organic phase and wherein said aqueous phase is recycled to the feed stream.

60. The pervaporation process of claim 1 wherein said pervaporation membrane may be reused.

61. The pervaporation process of claim 60 wherein said pervaporation membrane may be used for at least six months.

62. The pervaporation process of claim 61 wherein said pervaporation membrane may be used for at least one year.

63. A pervaporation process for the selective removal of acetone, butanol, or both, from an aqueous solution comprising the steps of (a) delivering an aqueous solution to the feed side of a pervaporation membrane, said pervaporation membrane having a first feed side and a second permeate side; (b) applying a driving force to cause permeation of the membrane by said aqueous solution; and (c) collecting the pervaporate exiting from said permeate side; wherein said aqueous solution comprises ethanol, and either acetone or butanol, or both acetone and butanol; wherein butanol selectivity is from about 100 to about 200 and/or acetone selectivity is from about 18 to about 40, and wherein ethanol selectivity is less than about 2; wherein said pervaporation membrane comprises silicalite particles embedded in a polymer matrix, wherein the silicalite:polymer weight ratio of said pervaporation membrane is from about 1.0 to about 2.5, wherein the membrane has a thickness of from about 300 µm to about 434 µm, and wherein the silicalite particles have a particle size of from about 3 µm to about 45 µm, a surface area of about 285 $m^2/g$, and a pore size of about 10 Å.

* * * * *